(12) United States Patent
Grajales

(10) Patent No.: US 11,924,365 B2
(45) Date of Patent: Mar. 5, 2024

(54) CLINICAL WORKFLOW, APPARATUS, METHOD AND SYSTEM FOR PROVIDING INDIRECT TO DIRECT TELEMEDICINE EYE EXAMINATIONS USING PORTABLE MEDICAL EQUIPMENTS CONNECTED VIA EMULATION SOFTWARE

(71) Applicant: Willis Dennis Grajales, Little Elm, TX (US)

(72) Inventor: Willis Dennis Grajales, Little Elm, TX (US)

( * ) Notice: Subject to any disclaimer, the term of this patent is extended or adjusted under 35 U.S.C. 154(b) by 193 days.

(21) Appl. No.: 17/352,329

(22) Filed: Jun. 20, 2021

(65) Prior Publication Data

US 2022/0392628 A1  Dec. 8, 2022

Related U.S. Application Data

(63) Continuation of application No. 17/180,789, filed on Feb. 20, 2021.

(60) Provisional application No. 62/982,040, filed on Feb. 26, 2020.

(51) Int. Cl.
| | |
|---|---|
| *H04M 1/72* | (2021.01) |
| *A61B 3/00* | (2006.01) |
| *A61B 3/028* | (2006.01) |
| *G06F 21/60* | (2013.01) |
| *G16H 10/60* | (2018.01) |
| *G16H 40/20* | (2018.01) |
| *G16H 40/67* | (2018.01) |
| *G16H 80/00* | (2018.01) |
| *H04M 1/72412* | (2021.01) |
| *G06F 3/0482* | (2013.01) |

(52) U.S. Cl.
CPC ...... *H04M 1/72412* (2021.01); *A61B 3/0033* (2013.01); *A61B 3/028* (2013.01); *G06F 21/602* (2013.01); *G16H 10/60* (2018.01); *G16H 40/20* (2018.01); *G16H 40/67* (2018.01); *G16H 80/00* (2018.01); *G06F 3/0482* (2013.01) CPC  H04M 1/72412; G16H 40/67; G16H 40/20; G16H 10/60; G16H 80/00; G06F 21/602; A61B 3/0033; A61B 3/028

See application file for complete search history.

(56) References Cited

U.S. PATENT DOCUMENTS

2018/0070820 A1 *  3/2018  Fried ............... G16H 40/67

* cited by examiner

*Primary Examiner* — Curtis B Odom
(74) *Attorney, Agent, or Firm* — Jacob M. Ward; Ward Law Office LLC

(57) ABSTRACT

The present disclosure relates to a clinical workflow, method, system and apparatus for performing an remote ocular health examination of a patient using medical equipment adapted to apparatus and emulating software and remote administration tool technology application. According to various embodiments portable medical equipment kit (OEK) can be assembled anywhere in the world connected to a computer. The MCB will have proprietary software to provide indirect to direct connection via layers. In an example embodiment, a method includes instructing a patient to position their eyes onto a camera where the image of the eyes are viewed on computer software. Where an on demand doctor can control the software that controls the cameras and review real time or near realtime the ocular images or videos via a indirect to direct connection to the main control base via a remote administration tool technology and emulating software using an internet connection.

10 Claims, 26 Drawing Sheets

Figure 1:
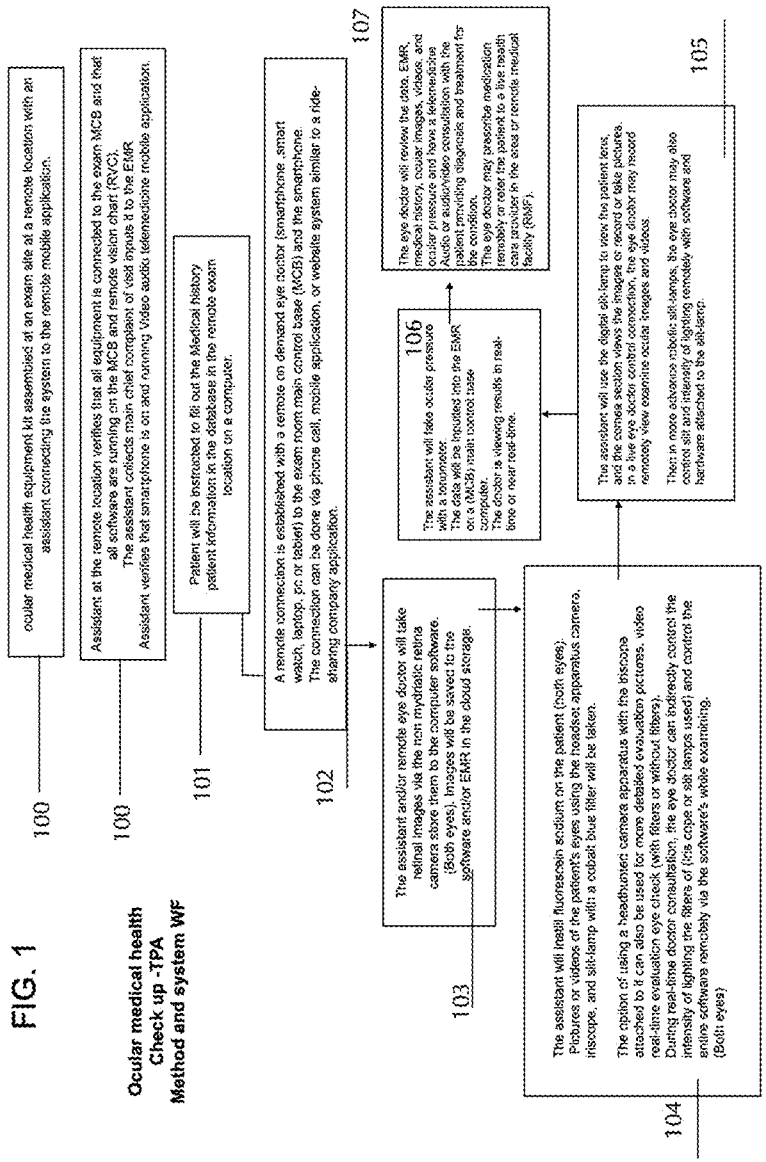

Ocular medical health
Check up -TPA
Method and system WF

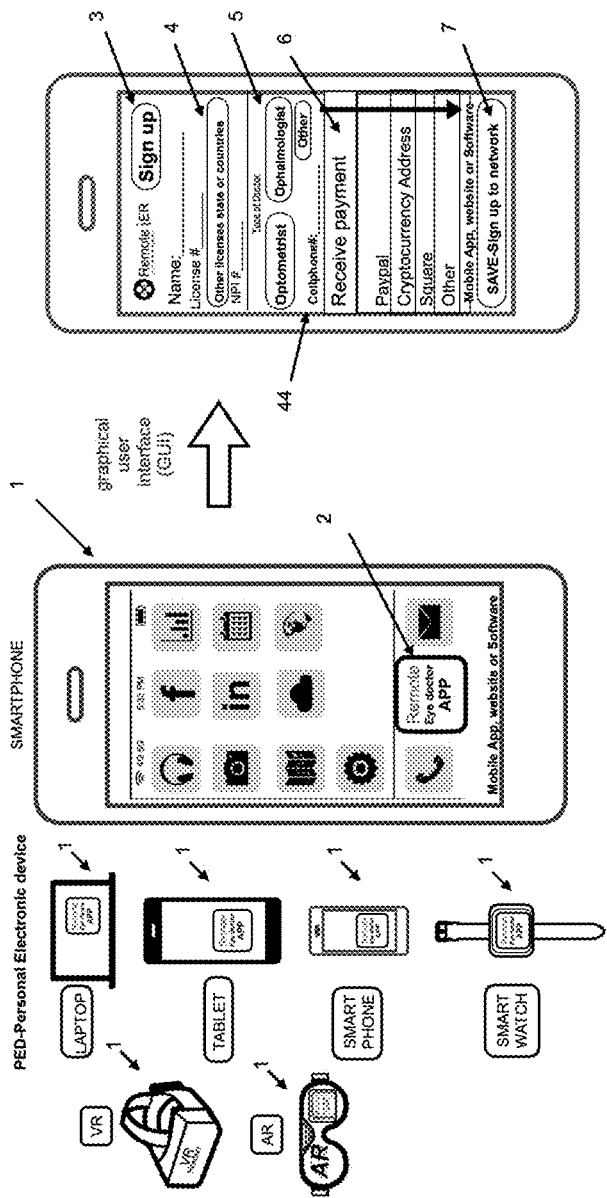

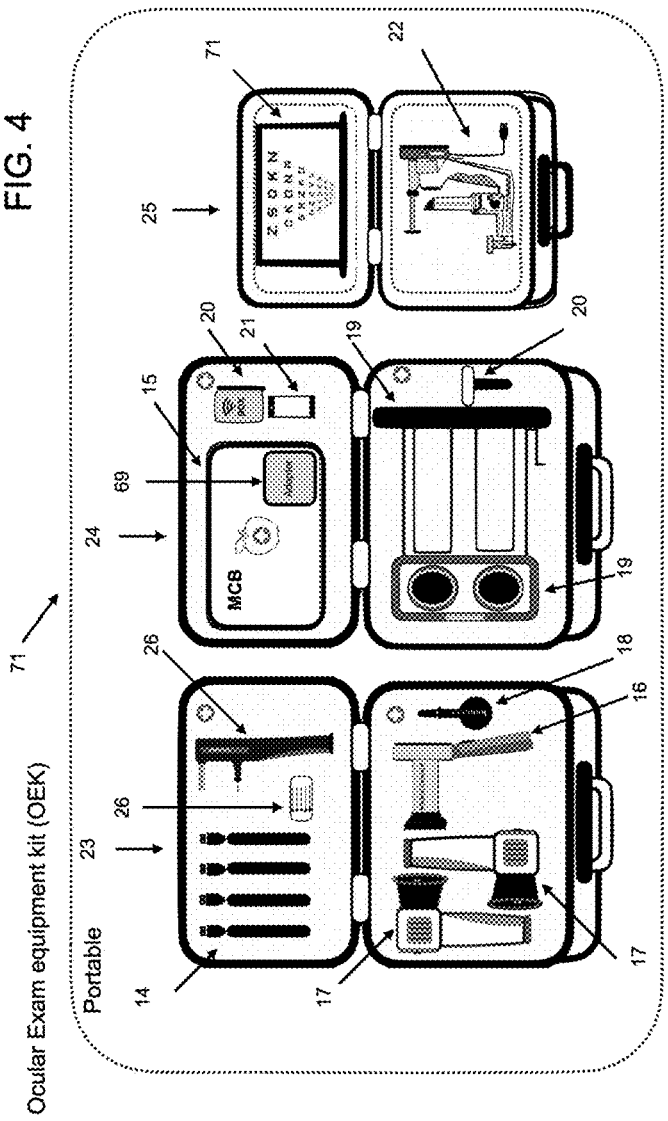

Ocular Exam equipment kit (OEK) upgrade 71

CLINICAL WORKFLOW, APPARATUS, METHOD AND SYSTEM FOR PROVIDING INDIRECT TO DIRECT TELEMEDICINE EYE EXAMINATIONS USING PORTABLE MEDICAL EQUIPMENTS CONNECTED VIA EMULATION SOFTWARE

RELATED APPLICATIONS

This U.S. Patent Application is a continuation of U.S. patent application Ser. No. 17/180,789 filed Feb. 20, 2021 titled "Worldwide indirect to direct on-demand eye doctor support refraction system via a remote administration tool mobile application on any portable electronic device with broadband wireless cellular network technology 4G, 5G, 6G or Wifi wireless network protocols to interconnect both systems.". which is a continuation of U.S. provisional patent application No. 62/982,040 filed Feb. 26, 2020 titled "Indirect to direct on demand eye doctor support refraction system via remote administration tool using any portable digital device by 4G, 5G, 6G or Wifi to interconnect both systems."

FIELD OF INVENTION

Embodiment of the present disclosure may include a computing device hub system configured to provide IoT capabilities to one or more medical devices via one or more connection to provide (ID) indirect to direct medical examinations, ocular health examination and a prescription to an examinee independent of location. Embodiments may also include a methods of using MCB system use of a one or more computer controller, interface controller, remote administration tool technology programs, an adapter apparatus (AA), emulating software, control software's and a mobile application to establish control and view connection to a medical devices interface. Embodiment may also include a system that may be modified to direct-direct control capabilities by connecting to the computing device associated with the medical device. Embodiment may also include a method of providing medical service via the MCB intermediary computer system pertain to the using an interface to control one or more software's including a medical device where medical device may be placed in any location.

Embodiments may also include a remote user using one or more Portable electronic devices, and a connection to an MCB and eye examination medical devices to simulate. Embodiments may also include an MCB comprising control and interface view of one or more medical devices. Embodiments may also include an MCB providing control and view of one or more interfaces to provide a remote telemedicine robotic consultation to an examinee (patient). Embodiments may also include a set casing comprising one r more ocular health medical equipment kit containing medical and non-medical devices that may be portable in nature. Embodiments may also include a OEK comprising one or more devices such as: digital slit-lamp, iriscope, a camera headset apparatus, wireless router smartphone, ocular tonometer and two portable computers. The OEK may be assembled in a mobile or non-mobile location to provide a platform for remote MCB medical examination system.

Embodiments may also include at least one of a MCB computing device that may have an ocular health camera, software, an apparatus with adapter, emulating software, electronic medical records software, mobile applications, and remote administration tool (RAT) and (RAS) remote access software applications. Embodiments may also include computing device executing software that enables it to work as a vision chart, duo chrome and astigmatic dial chart using software. Embodiments may also include a smartphone wireless networks or WIFI wireless networks provide a remote user to provide indirect to direct real time or near real time telemedicine ocular health screening or examination to a remote examinee anywhere in the world with the connection to portable or non-portable medical devices.

BACKGROUND OF INVENTION

There is a disparity of vision medical and eye health care coverage worldwide, not because of a shortage of health care providers, but due to a shortage of health care providers that are within proximity to a patients. Uneven health care and ocular health coverage leads to underserved populations from obtaining much needed emergency health examination, which decreases these populations overall quality of life and limits their productive abilities. Examples of locations in need may be at least one of: an emergency room, clinics, mobile clinics, government agencies, astronaut space stations, hospitals, optical, optometric practices, and ophthalmology practices. All examples struggle to find a cost-effective strategy that may supply people with adequate and easily accessible, twenty four hours, medical, emergency ocular health screenings and examination from a professional health care provider.

The present system and method seeks to provide adequate and easily accessible opportunities for underserved populations to obtain precise, tailored telemedicine ocular health screenings and examinations from a remote health care provider independent of time zone and space. The system and method proposes to achieve this using an MCB computing device, remote administration tool technology, adapters, software's, telemedicine video audio connection, mobile applications, emulating software's, remote access, remote-control, screen viewing to interconnect with an health care provider computing device via ethernet, Wi-Fi or cellphone wireless networks worldwide.

BRIEF DESCRIPTIONS OF THE DRAWINGS

FIG. 1—illustrates a workflow diagram of a method for performing ocular medical health check-ups (PA) Therapeutic pharmaceutical agent check-ups.

Figure 1A:
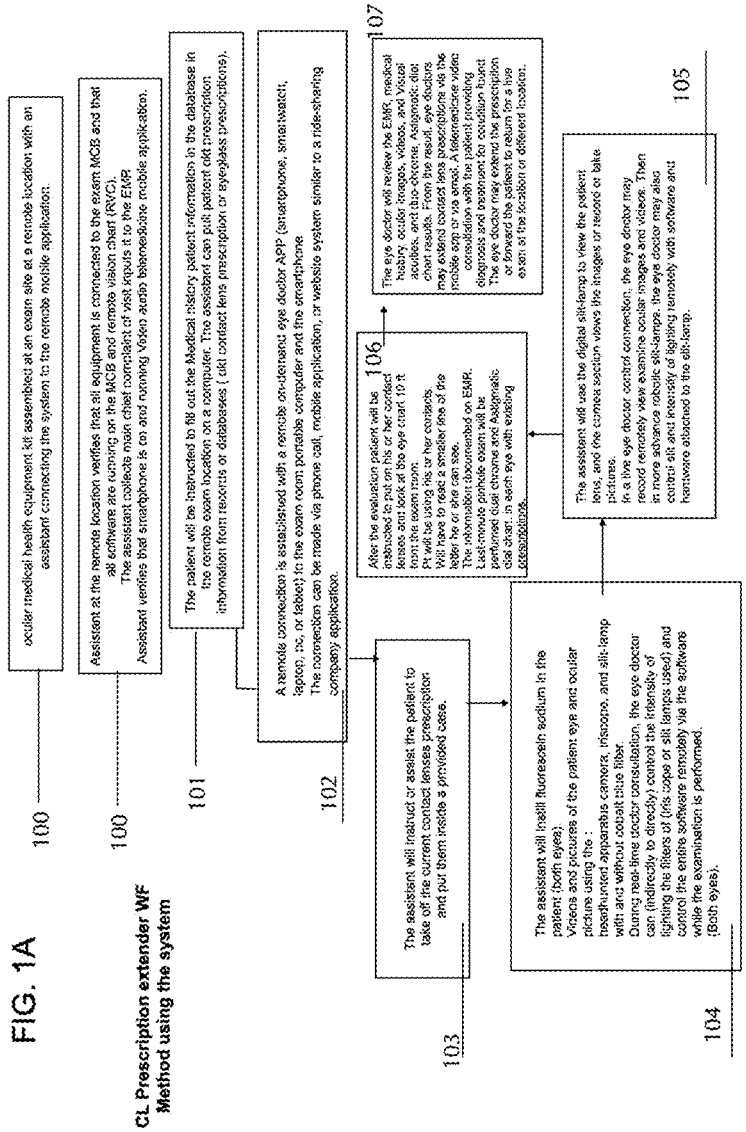

FIG. 1A—illustrates a workflow diagram of a method for performing a contact lens prescription extension.

FIG. 2—illustrates an embodiment of a group of portable electronic device PED that may be used by a remote user (controller) to provide medical service via controlling of a emulated medical device interface. The proposed devices comprise at least one or a combination of: a smartphone, virtual reality headsets, augmented reality headsets, VR/AR, smartwatches, laptops, or any computer system. The website or mobile application may display a graphical user interface with sign-up menu to log in, section for a remote user (health care professional) sign up for social network system. Section may request the name health care providers license numbers, state, country, provider identification number, (NPI), type of health care provider, cellphone number, and alternative to receive payment for remote medical service.

Figure 3:
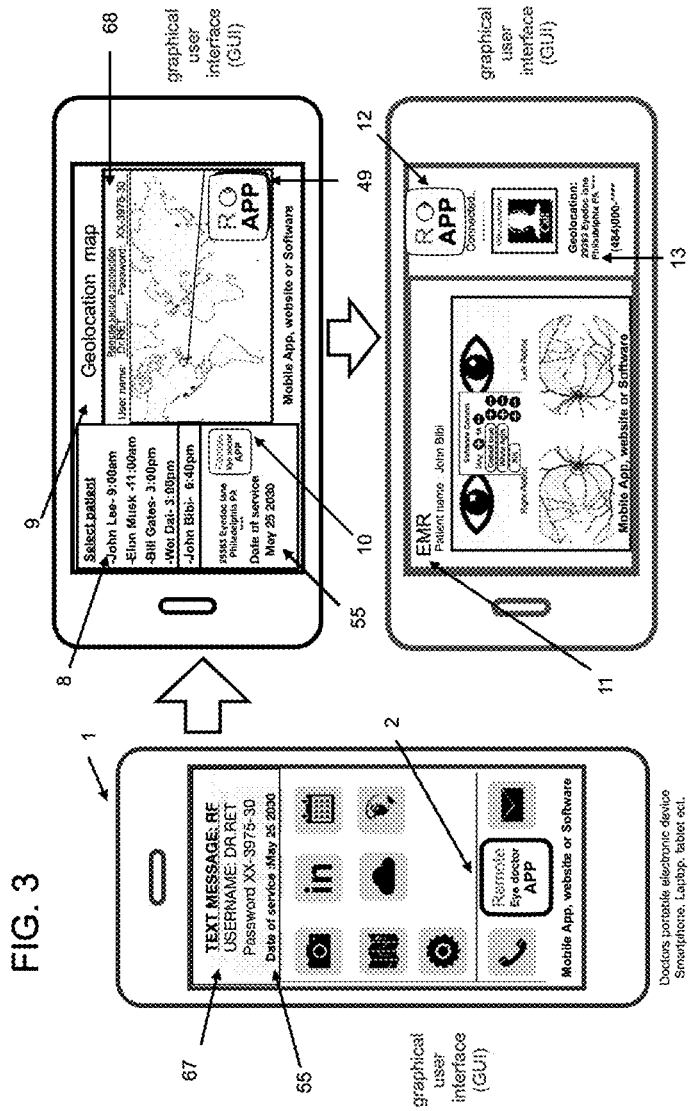

FIG. 3—Illustrates embodiments of one of a remote user portable electronic devices displaying the graphical user interface of one or more computing devices. Where connecting the device and location of the RMF. Display of the location and time for needed remote user (health care provider) and examinee booking match, where the remote user (controller) may select the date, time, and location to provide service and receive an electronic message confirmation or text message of the user name, password and day and time to provide service, where the remote user may connect to the (MCB) to view control at least one of a plurality of medical devices and computing devices via at least one MCB computer controller system.

FIG. 4—Illustrates a pictorial diagram embodiment of a group of ocular examination equipment kits and secure casing that are portable in nature and can be sent or receive anywhere in the world to establish a remote medical facility setup, where the ocular examination kit may have a at least one a wired connection devices, wireless connection device, two iris-copes one (MCB) computer system, fluorescein sodium kit, remote vision chart system portable slit-lamp with or without robotic adapters and computer system, cellphone wireless router system, (MCB) adapter and a smartphone.

Figure 4A:
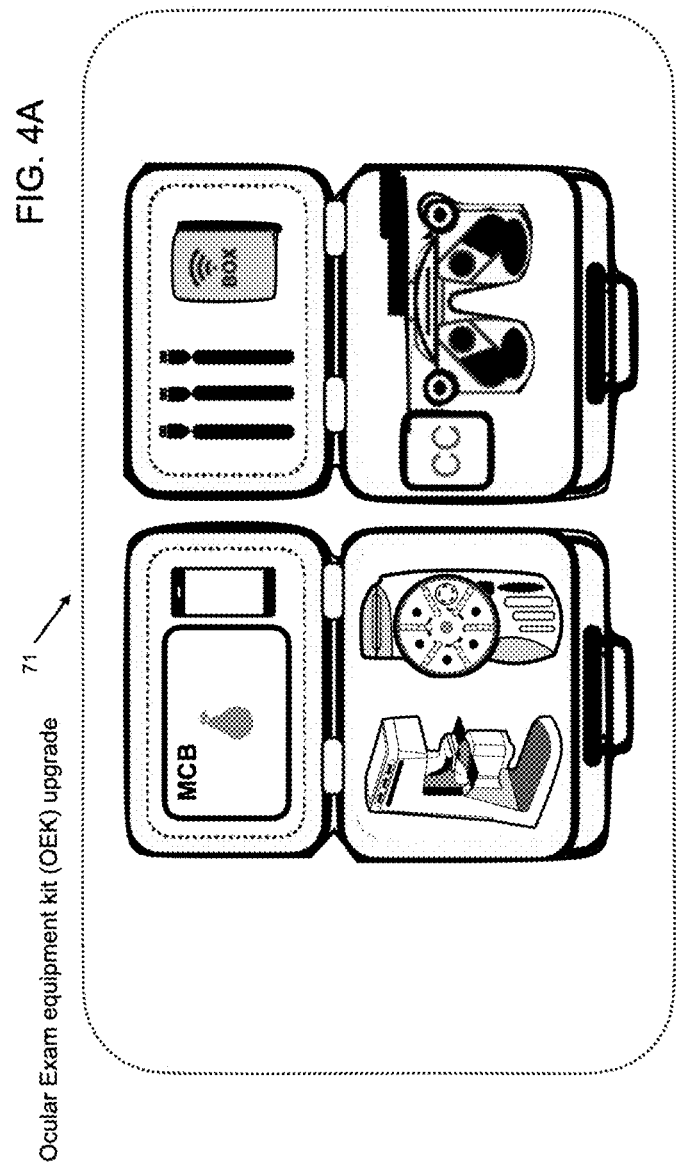

FIG. 4A—Illustrate pictorial diagram embodiment of an ocular examination equipment kits and secure casing that are portable in nature and can be sent or receive anywhere to establish a remote medical facility setup. Where the ocular examination kit may have a plurality of wired cable connection devices, iris-copes, at least one extra (MCB), an automatic digital lens-meter, at least one cellphone wireless router, smartphone with an operating system and at least one phoropter or subjective refractor apparatus. Where the refractor and phoropters may be an automatic objective refractor, an digital phoropter, subjective refraction equipment, variable focus liquid lens refractor, and/or liquid lens subjective refractor.

Figure 5:
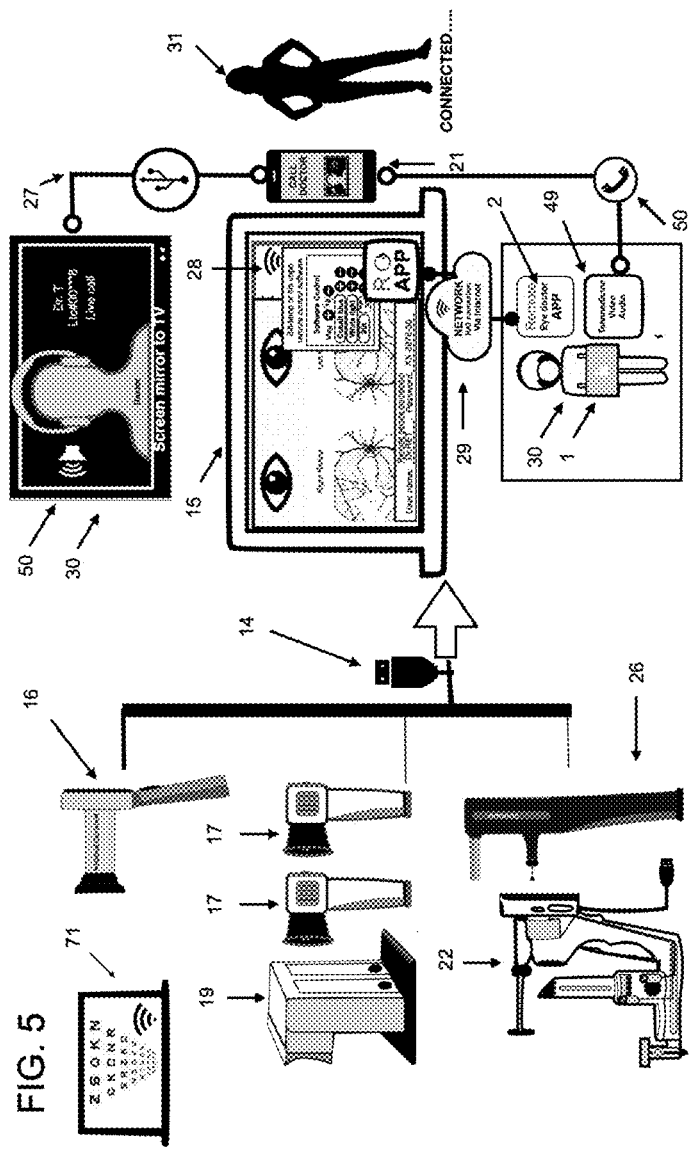

FIG. 5—Illustrate pictorial diagram embodiment of the connection of the ocular examination kits a medical devices that may be connected to a one or computing devices and (MCB computing device) in the remote medical facility anywhere. Where a remote administration tool, screen share, screen control and screen mirror connection are established between the remote distance remote user computing device (health care professional) and the remote medical facility via the (MCB) and a smartphone connection via a HIPPA compliant audio video or text call where audio video call is mirrored to a display screen.

Figure 6:
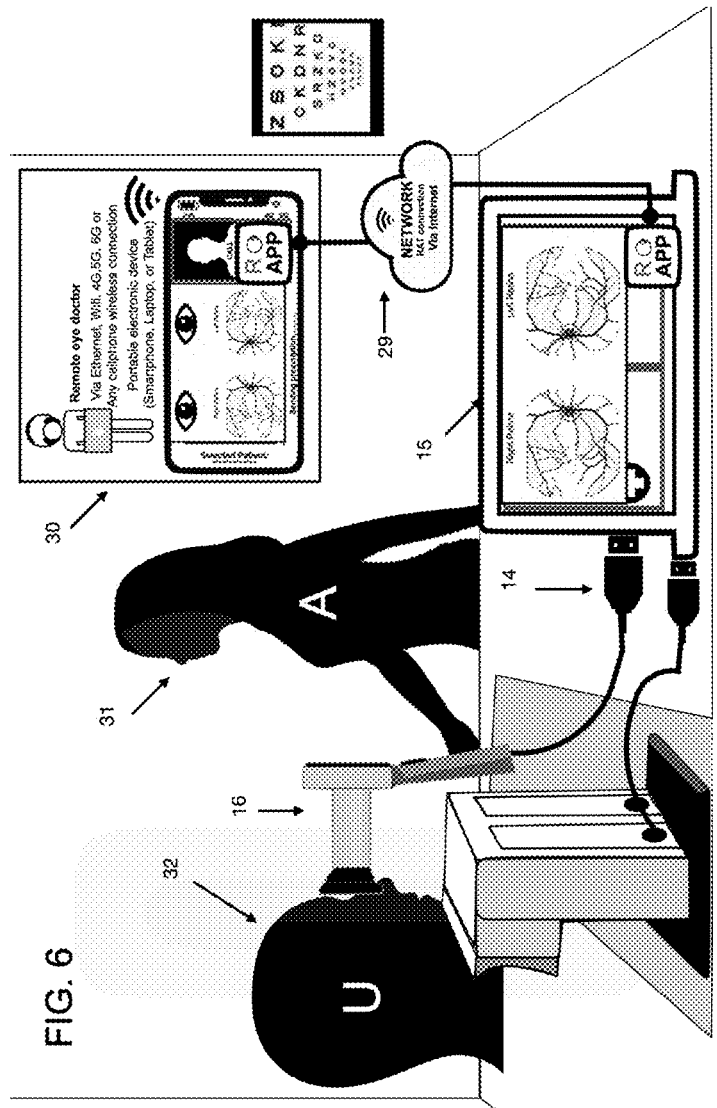

FIG. 6—Illustrate pictorial diagram embodiment assistant connecting with live remote user (HCP) where the (Assistant) and remote user may collect retinal images via "store and forward" technique or real-time remote control of the software's the controls the retinal camera images via real-time Tele-imaging. A method of using remote administration tool, emulating software's, screen share, screen control, and screen mirror software's via a the any type of internet network or network to perform ocular and vision chart exam for an examinee.

Figure 7:
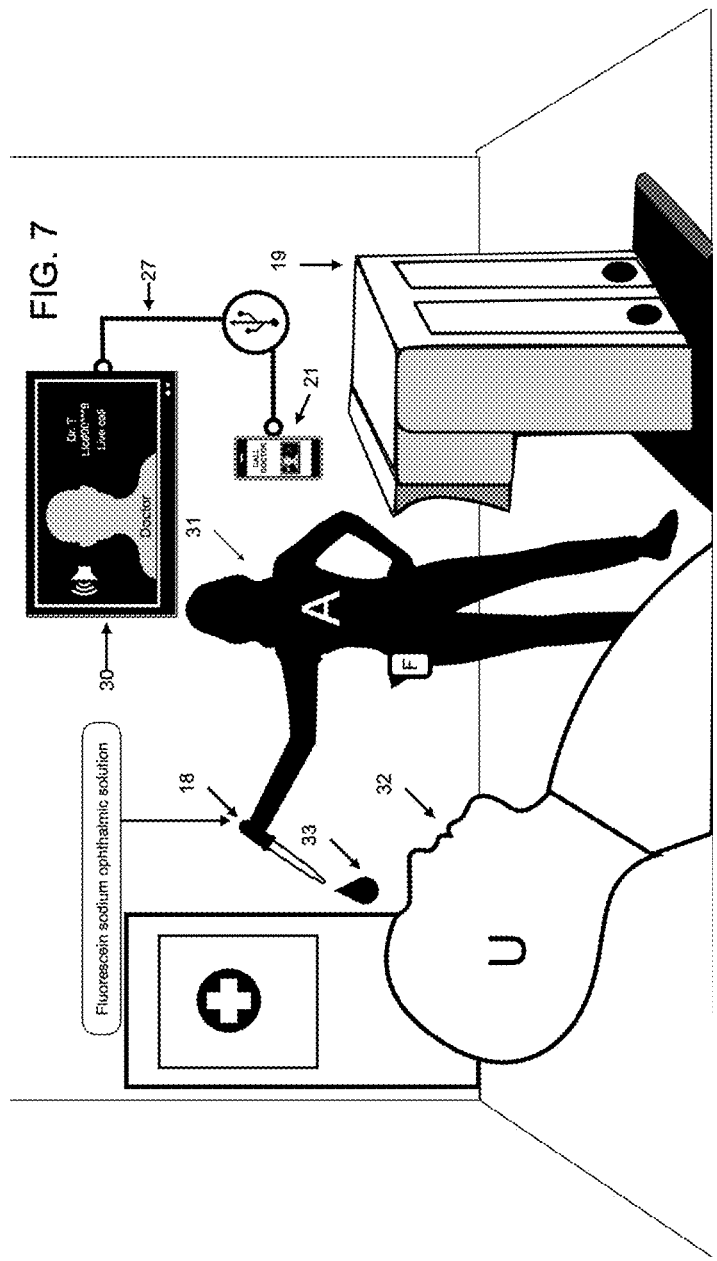

FIG. 7—Illustrate pictorial diagram embodiment of a method performing a real-time Fluorescein sodium cornea staining examination using real-time tele-imaging via remote administration tool, emulating software, screen share, screen control, and screen mirror software via the internet network or network. With iris copes camera, that has cobalt blue filter. Where the iris copes can be installed into a head-mounted apparatus for the (assistant, HCP health care provider, human and/or technician) and remote user (eye doctor or HCP) to achieve a binocular view of external ocular images.

Figure 8:
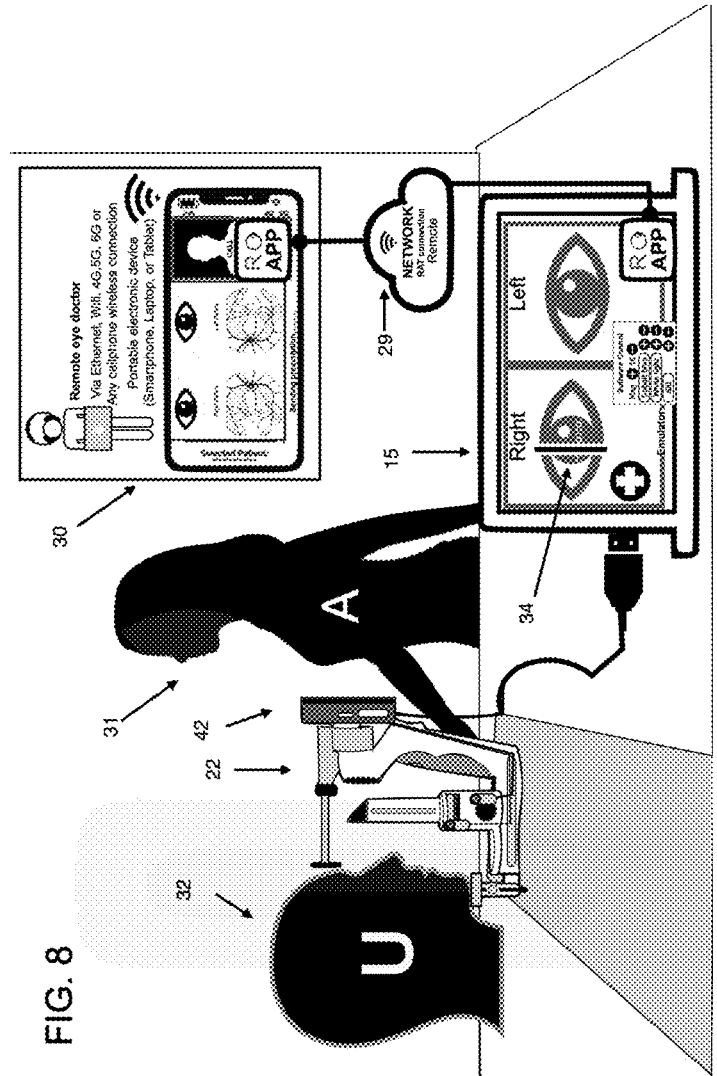

FIG. 8—Illustrate pictorial diagram embodiment of method to perform a remote slit-lamp evaluation via the slit lamps first computer adapted to the (MCB) secondary computer where a remote user (health care provider) may real-time view the images, videos and may control parts of a slit-lamp robotic to view ocular adnexa health of the patient one or two eyes of the examinee. Where the robotic adapted slit-lamp may be controlled or viewed by a remote user or assistant using slit, magnification, angles, filters, and/or angles.

Figure 9:
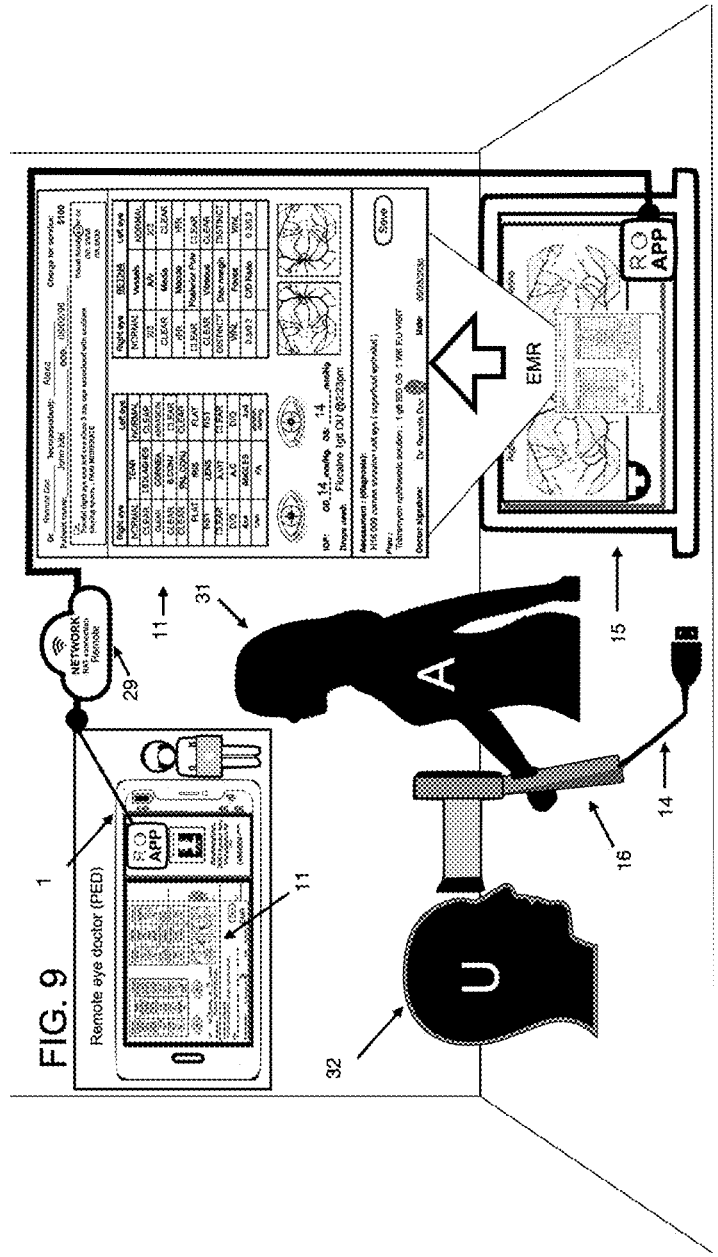

FIG. 9—Illustrate a pictorial diagram embodiment of an assistant in a location simultaneously taking retinal images. Where the remote user may also view, control, and types of patient data from examination to the EMR via the one or more portable electronic device in real-time. The real-time connection done via one or more remote administration tool, emulating software, screen share, screen control, and screen mirror software via any internet network or network.

Figure 10:
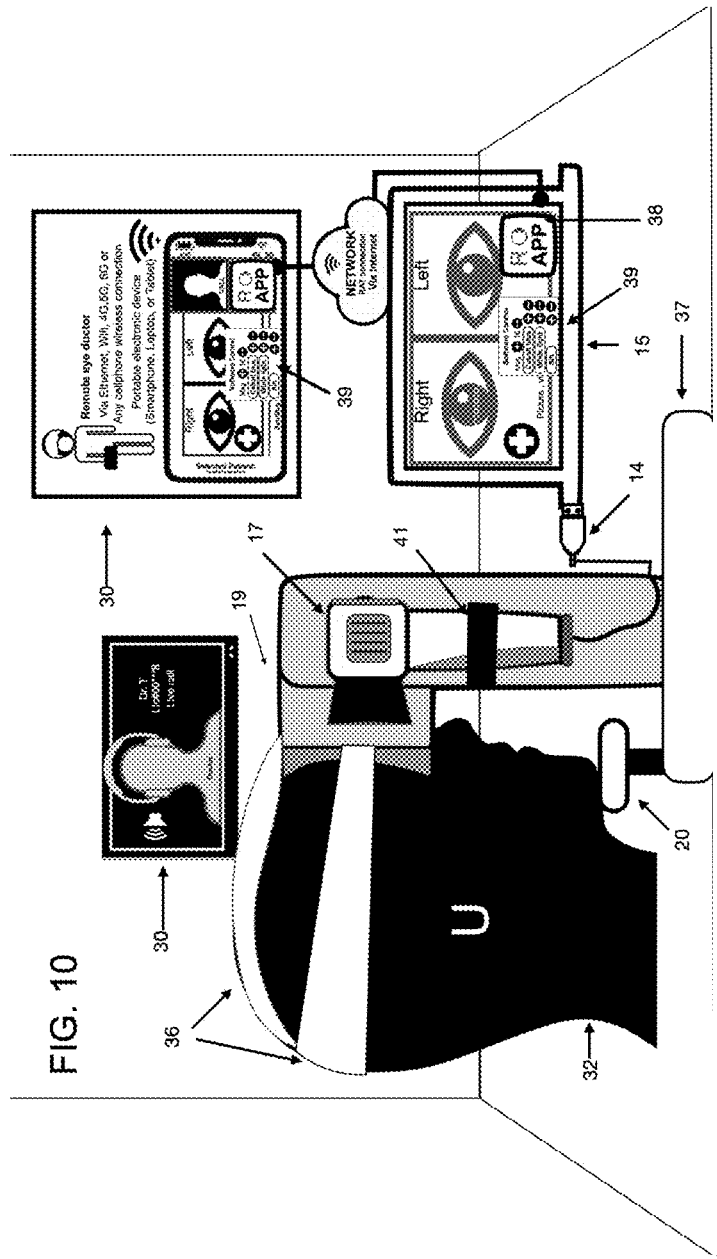

FIG. 10—Illustrate pictorial diagram embodiment of a head-mounted ocular camera apparatus adapted to two iris-copes (ocular camera system). The ocular cameras relaying images to the (MCB) where remote user (health care provider) may visualize fine details such as eye movements when testing for extra-ocular motor function and pupil size and test for pupillary reflexes. To detecting strabismus, disorders of the eyelids, conjunctival disorders via real-time remote administration tool, emulating software, screen share, screen control, screen recording, and screen mirror software via the wireless or non-wireless internet network. Where the video audio call may be screen mirrored from the portable computing device PED to a smart display.

Figure 11:
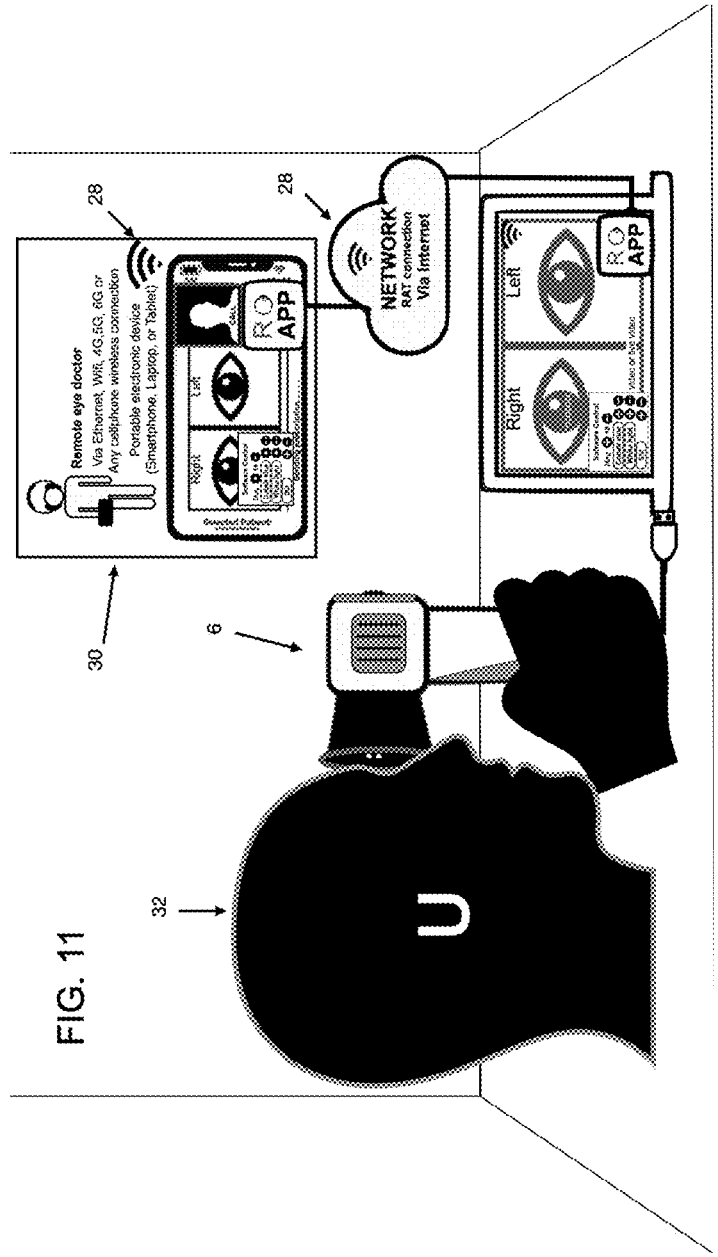

FIG. 11—Illustrate pictorial diagram embodiment of a examinee as an assistant holding a modified iris-cope or external ocular camera with filters. The images are sent to a secondary computer (MCB) where the remote user is connected via real-time remote administration tool, emulating software, screen share, screen control, and screen mirror software's via the internet network or network. Where the remote user may control a software's that control the lighting filters and zoom mechanism of the iris-cope or ocular camera. Where the interconnection control and view are from remote eye doctor computing electronic device and are used to view, document, record and diagnose disorders of the eyelids, conjunctival disorders, and external ocular structures of the eye.

Figure 12:
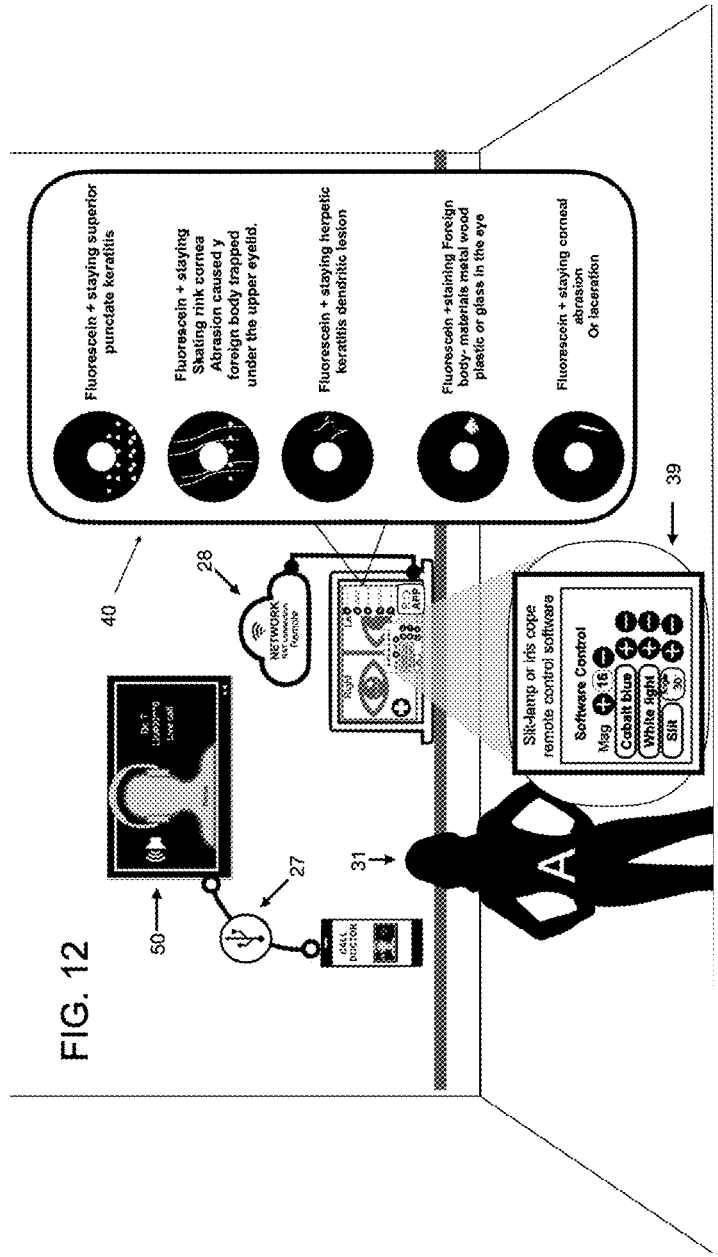

FIG. 12—Illustrate a pictorial diagram embodiment of method of doing a remote corneal fluorescein staining evaluation. An assistant or examinee may instill one drop of fluorescein sodium dye to one or more eyes of an examinee. Where the examinee eyes health may be examined, viewed, and recorded by a remote user. A remote user (eye doctor or HCP) examining for cornea for damages as seen via a interface of external ocular camera, iris cope, ocular camera headset apparatus, or slit lamp. Where an the eye doctor is connected via a computing device and real-time screen mirrored to location vision display. Where the eye doctor can view the images saved on the of patient cornea and conjunctival damage with and without fluorescein staining dye and with without cobalt picture using real-time remote administration tool, emulating software's, screen share, screen control and screen mirror software's and an internet network or network connection. Where the first one image from top to bottom are fluorescein staining of the cornea via a cobalt blue filter, the top first one is superior punctate keratitis, second is staying skating rink core abrasion caused by possible trapped foreign body trapped under the upper eyelid, third is staining foreign body material metal, wood plastic or glass in the cornea, and fourth is staying corneal abrasion or laceration.

Figure 13:
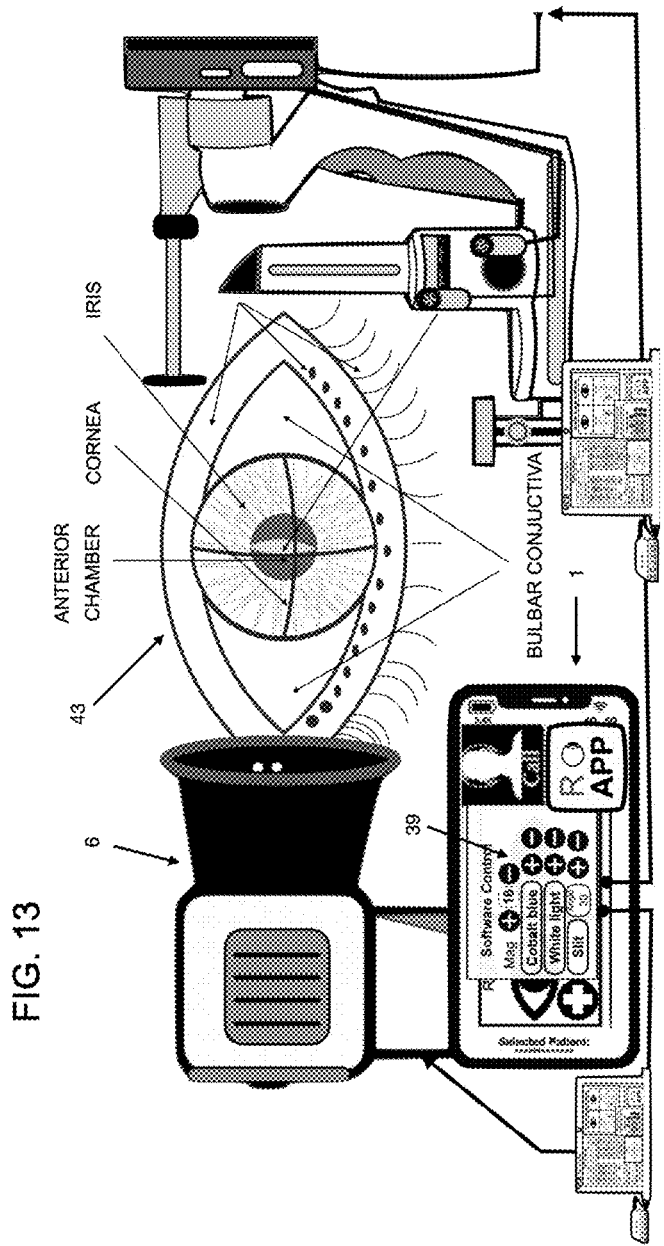

FIG. 13—Illustrate a pictorial diagram embodiment of an iris-cope with its part and its lights, cup assembly and a portable digital slit-lamp with a robotic adapter configured for remote control software to control parts of a slit lamp. Where an eye doctor in a remote location can con both devices simultaneously via control of the (MCB) second computer using tele-imaging control software via remote administration tool, emulating software's, screen share, screen control and screen mirror software's via the internet network or network. Where the eye doctor can control via interface the electronic device magnification or zoom of the iris cope, cobalt blue filter lights, white light intensity, slit, and angle. Where the eye doctor may take picture, record images via the software or while viewing real-time.

Figure 14:
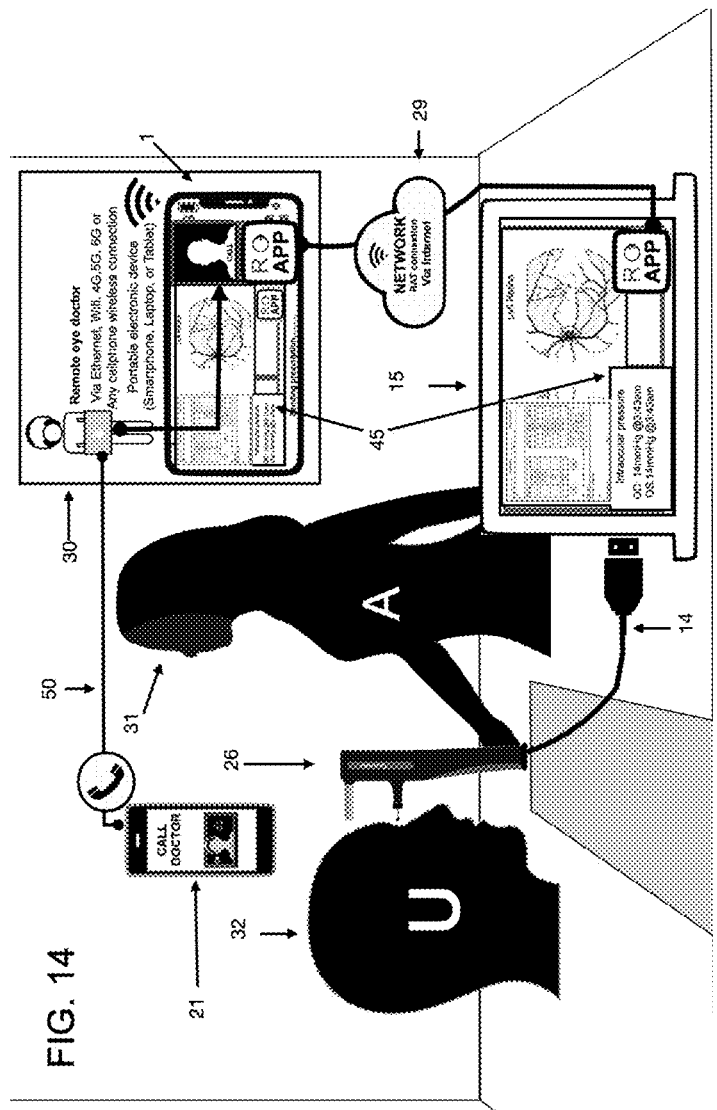

FIG. 14—Illustrate pictorial diagram embodiment an assistant takes ocular pressure via a portable handheld ocular pressure tonometer. Where the pressure is inputted by the doctor via his portable electronic device (smartphone). Where the (Assistant) can also input the information in the electronic medical record on the (MCB). Where the remote user may be connected via video audio call with a smartphone at the same time.

Figure 15:
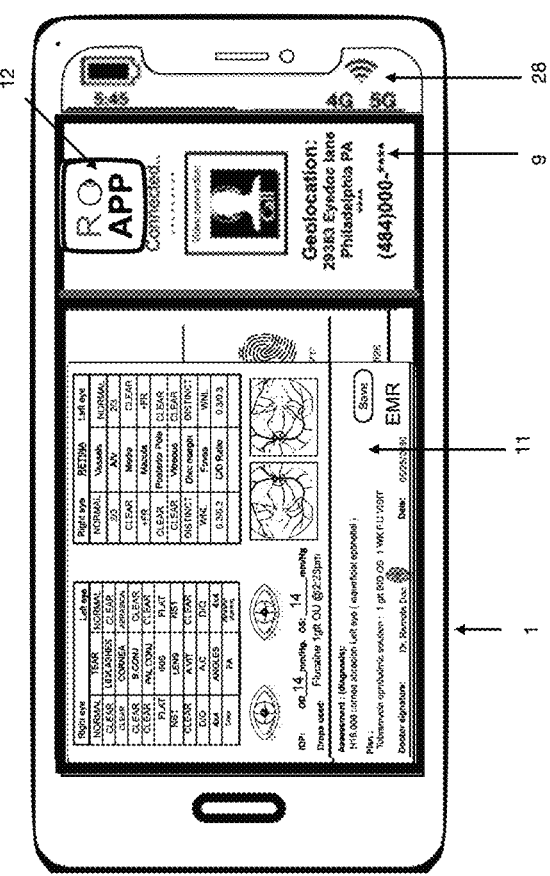

FIG. 15—Illustrate pictorial diagram embodiment of a remote user portable electronic device connected to the (MCB) via the mobile application, program, or website. Where the remote eye doctor can view, and control the electronic medical record, review, input information, fill out results, fill out diagnosis, plan treatment and sign electronically. Where the application may have the call video conference interface open and the geolocation or location data pertaining to the remote medical facility.

Figure 16:
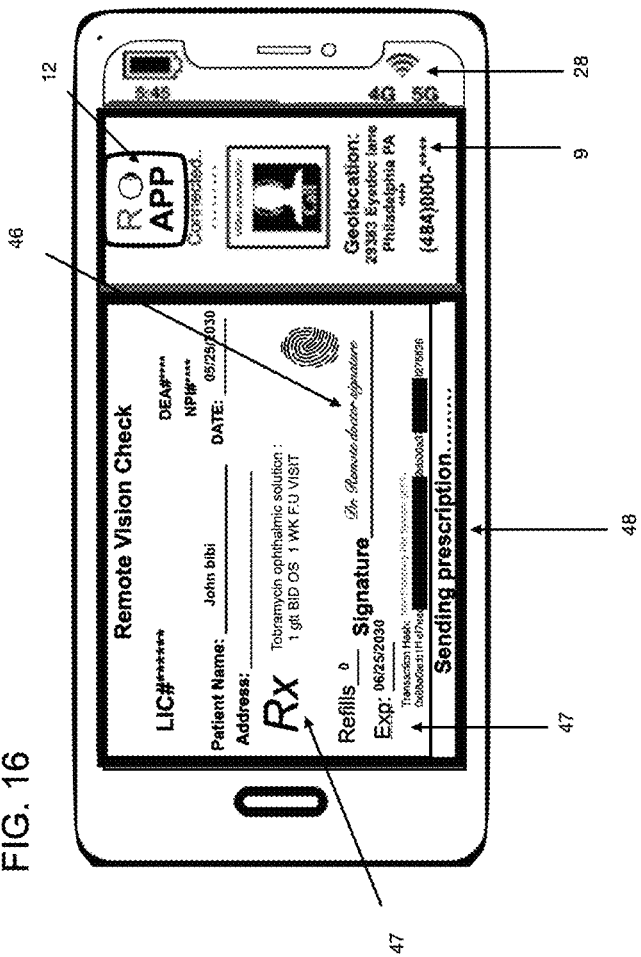

FIG. 16—Illustrate pictorial diagram embodiment Illustrates a remote user (eye doctor or controller) portable electronic device running the mobile application where the eye doctor is filling out an electronic prescription for a patient, filling out name, date, NPI, License number, expiration date, and signing with an electronic signature. Where in authentication on blockchain technology a prescription system, a transaction hash may be displayed on the bottom.

Figure 17:
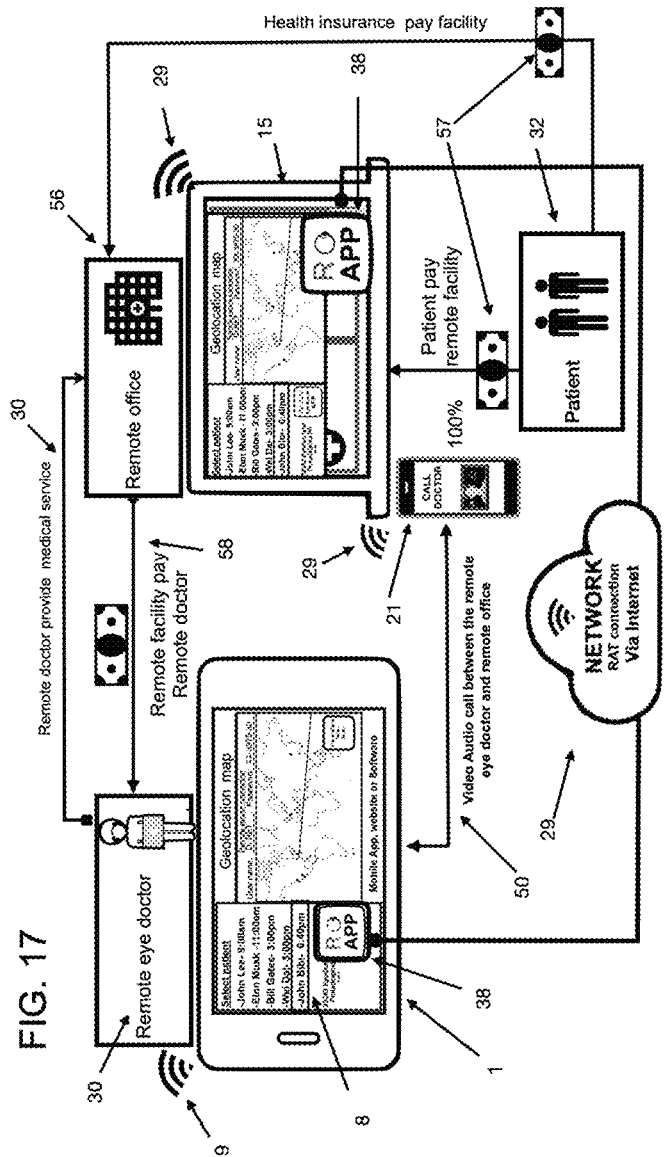

FIG. 17—Illustrate a pictorial diagram embodiment of a remote user providing service to a remote medical facility via the mobile application, program and/or website. The eye doctor is connected to the network and established a video audio call where the eye doctor is connected to the (MCB) main control base via remote administration tool technology, screen share, and screen control. Where after receiving service, the patient can pay the remote facility directly or via health insurance. Where the remote user may receive payment for the service he rendered by the remote medical facility via the application, program, or website.

Figure 18:
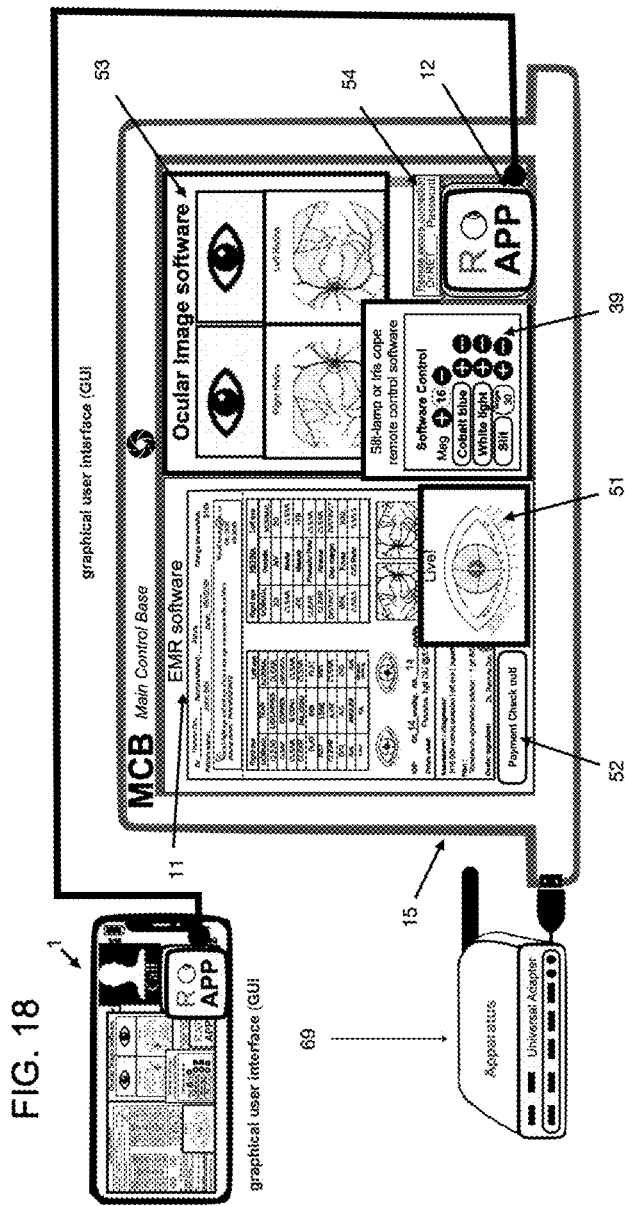

FIG. 18—Illustrate pictorial diagram embodiment of an (MCB) main control base computer system smart hub. The MCB displaying an adapter apparatus and an emulating interface connection. Where the (MCB) is connected to multiple medical devices and eye examination equipment and is able to view all user interfaces of all equipment connected ocular image software, slit-lamp control, lice slit lamp or iris cope video, payment checkout system, and its Electronic medical record system from one interface. where a remote user (eye doctor) portable electronic device may connect via one or more network to view and control the (MCB) interface via remote administration tool, screen share, screen mirror, and screen control.

Figure 19:
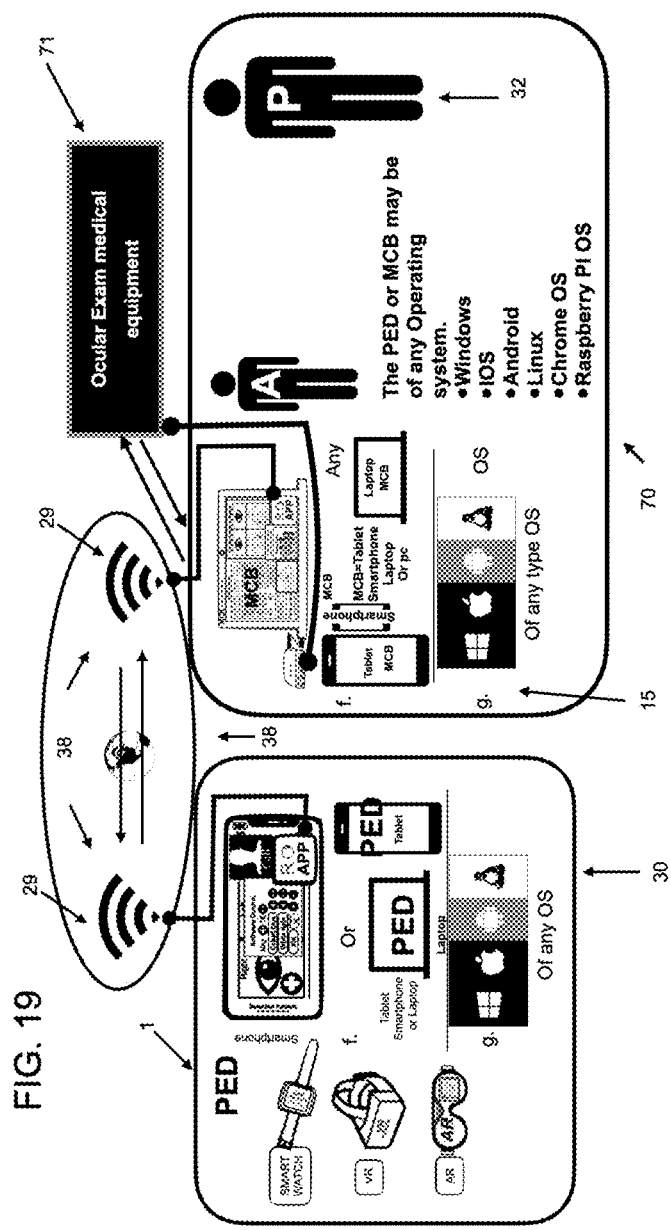

FIG. 19—Illustrate pictorial diagram embodiment of a group of remote users (HCP) types of portable electronic devices that may be used. A method of executing a RAT application to connect to at least one (MCB) interface. The connection aiding in control and screen view one or more medical device interfaces. Where the remote user portable electronic devices may be a virtual reality headset, smartwatch, augmented reality headset, AR/VR, Laptop, smartphone. Where any of the MCB and PED may run any operating system including Windows, apple, android, Linux, or any other operating system. Where the connection from remote user portable electronic device comprises a connection to connect to an (MCB) via a combination of software's. Where the (MCB) main control base may be a tablet, Laptop, smartphone, or any computing personal computer. Where the (MCB) is connected to a computing device associated to medical device. Where the (MCB) is connected via an Internet network or local area network to at least one remote user PED. Where a patient (examinee) is at the remote medical facility waiting and being examined.

Figure 20:
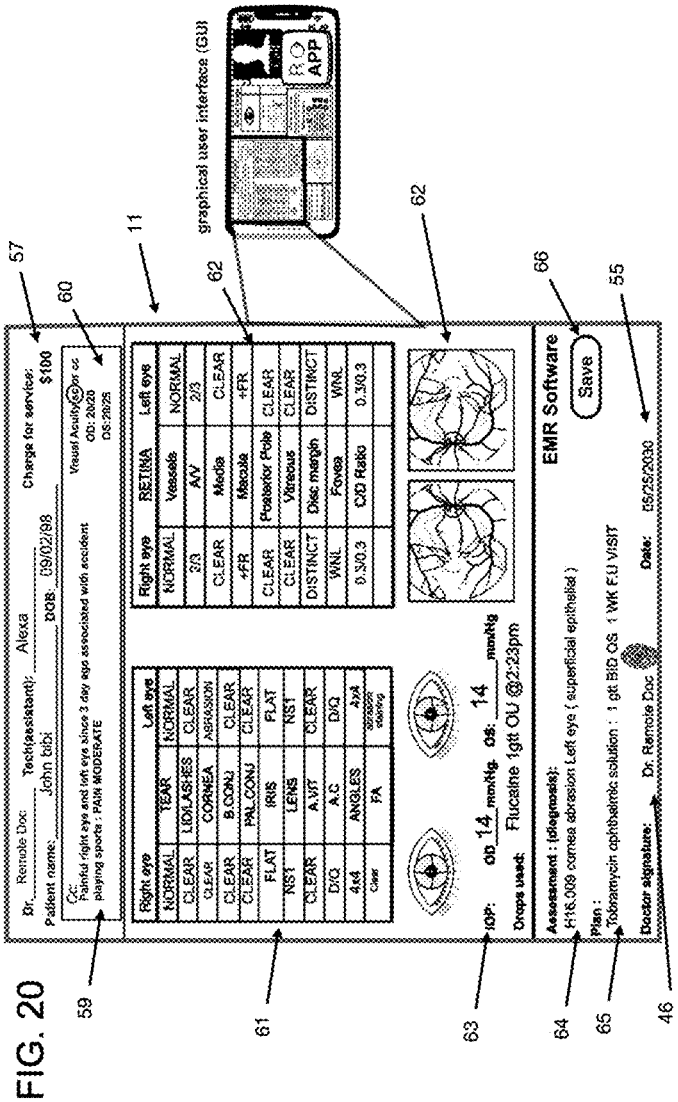

FIG. 20—Illustrates a pictorial diagram embodiment of an (EMR) electronic medical record running on the main control base user interface. Where (MCB) user interface, it is viewed, controlled, and edited by a remote eye doctor or controller's portable electronic device (smartphone). Where the eye doctor can view, control, and edit the electronic medical record system remotely and sign remotely, save documents remotely via mobile application with remote administration tool, screen view, screen mirror, and screen interface control.

Figure 21:
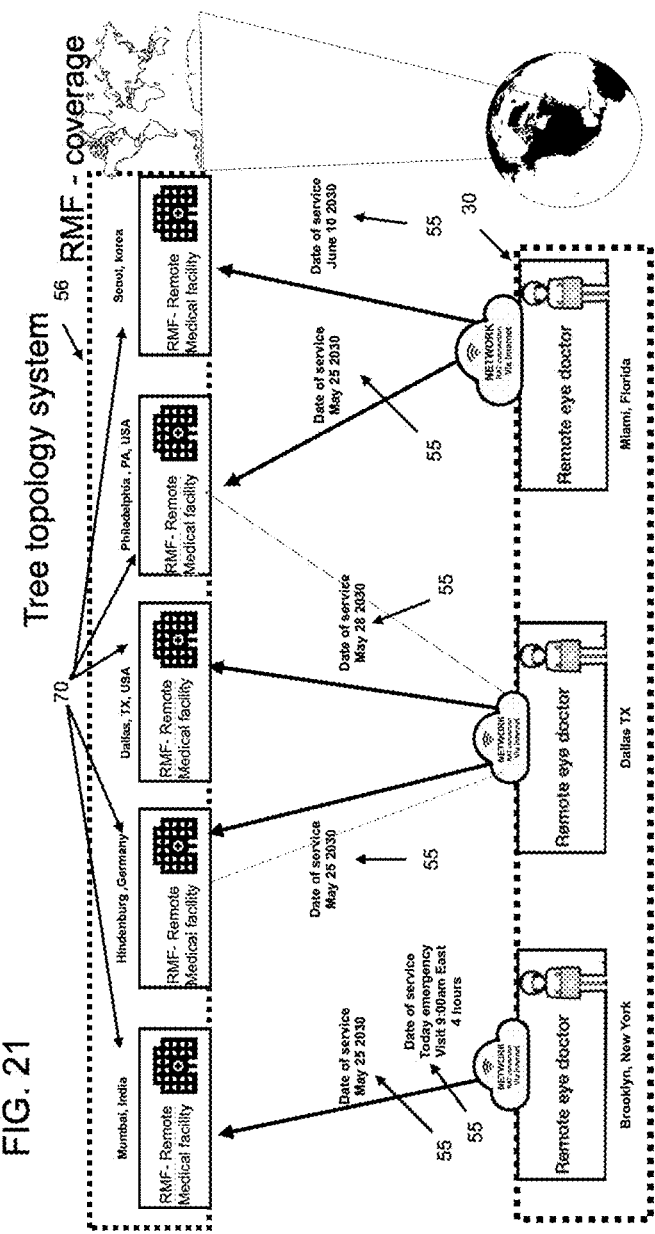

FIG. 21—Illustrate pictorial diagram embodiment Illustrates a network of remote medical facilities all over the world and outer space that may be connected to remote eye doctors or controllers anywhere in the world. Where remote eye doctor can schedule date, time, and location to provide service via the mobile application, program, or website via the network. Where the remote medical facility may or may not have all its equipment connected to the (MCB).

Figure 22:
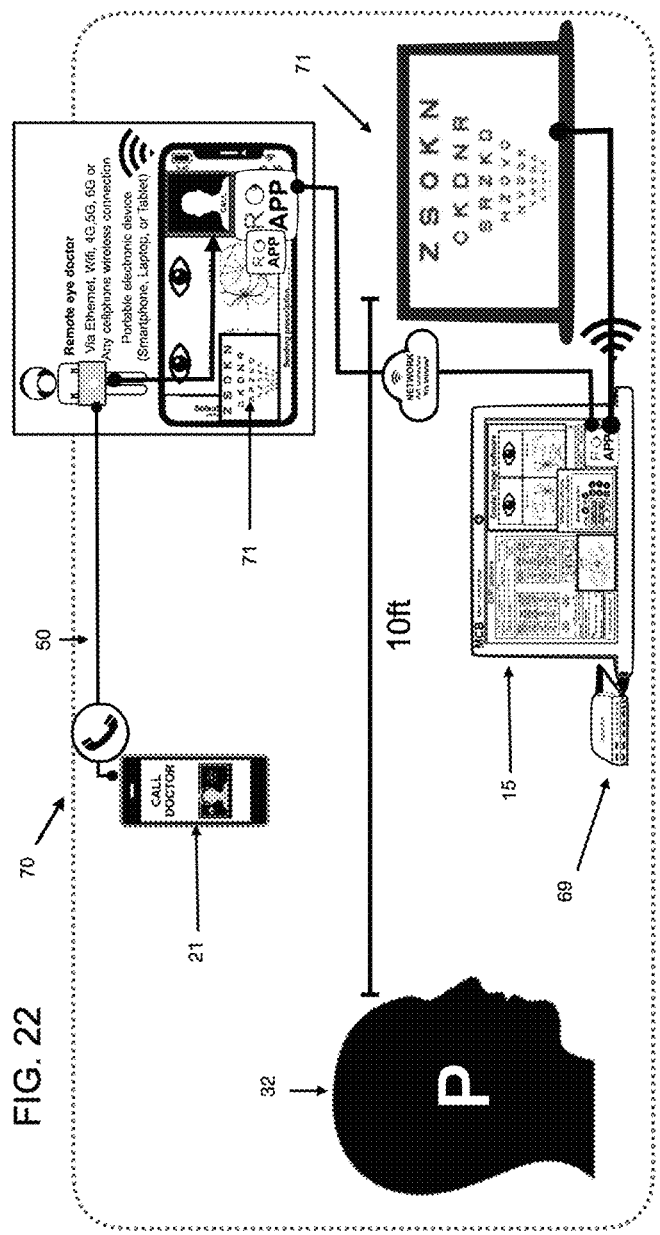

FIG. 22—Illustrates a pictorial diagram embodiment of a patient (examinee) in a remote medical facility or location viewing a remote vision acuity chart displayed onto the interface of computing device system. Where the computing device interface vision chart is connected to the remote user device and or the (MCB). Where remote user may control the vision chart interface via at least one of an adapter, infrared, Bluetooth, WIFI, LAN or any wired or non-wired configuration. Where a remote user (eye doctor or controller) may control the vision chart via the (MCB), and established video audio call to the patient (examinee) via the remote facility computing device or PED.

Figure 23:
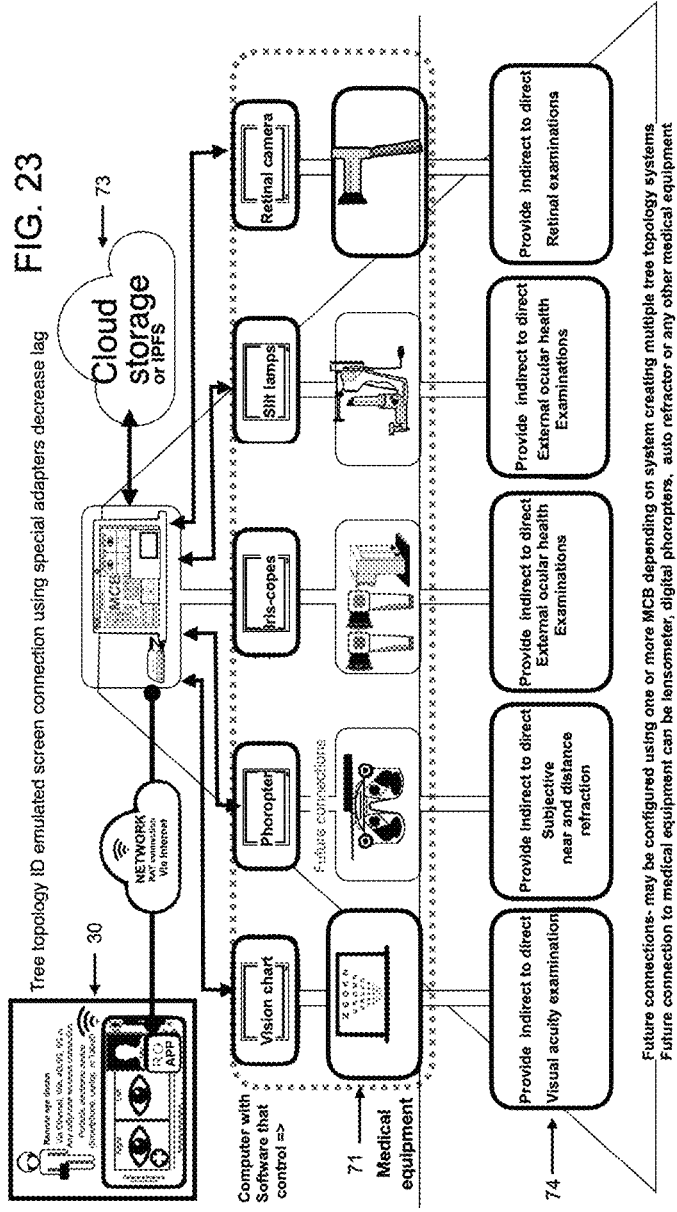

FIG. 23—Illustrate a pictorial diagram embodiment Illustrates a way to connect the systems via one or more types of topologies configuration. Where connection may be via wired or wireless connection to establish indirect to direct connection. Where at least one (MCB) main control base may be connected to control and view one or more medical devices interfaces concurrently via one or more networks. The MCB using software's, an adapter, emulating software, remote administration tool technology, emulating software, screen share, screen control, and screen mirror. A remote users computing device PED commissioned to control the (MCB) main control base user interfaces over a network. An extra configuration to access cloud storage, files sharing system and/or IPFS for data and/or medical data.

Figure 24:
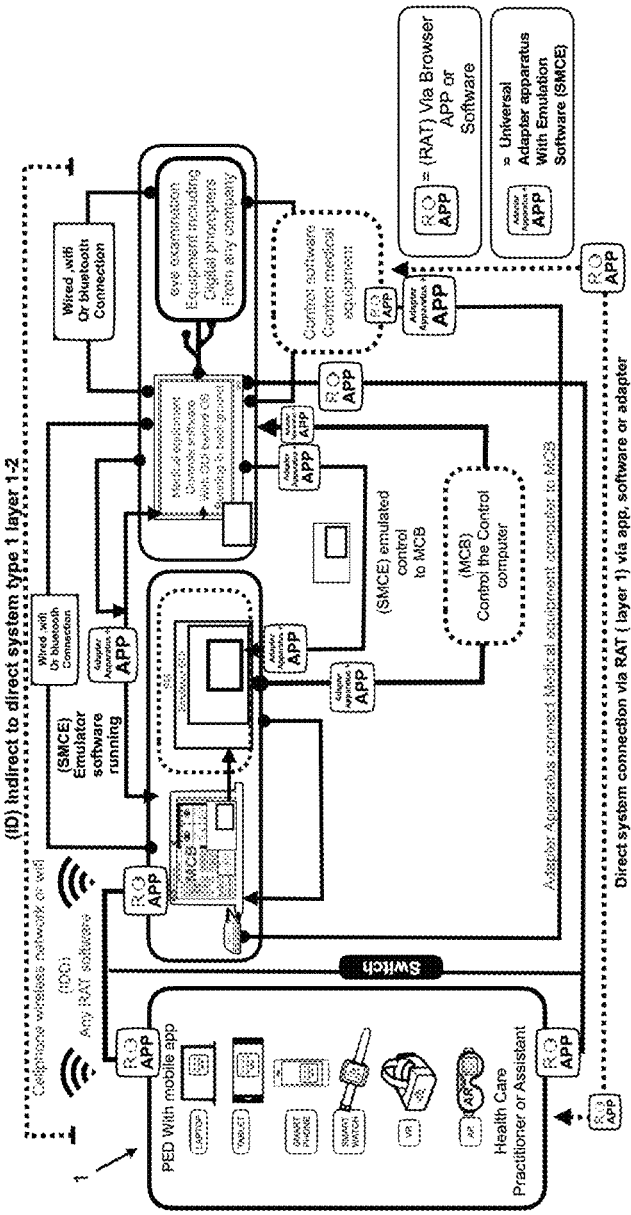

FIG. 24—Illustrate pictorial diagram embodiment Illustrates via a connection used to connect to at least one medical device interface. Where the medical device may be an embedded system or non-embedded computer system. Where the computing is configured to control at least one medical device directly via wireless or wired connection. Where computer is connected to a secondary computer system called the (MCB) or smart hub. Where at least one first computer is connected to the (MCB). Where the first computer interface is emulated on to MCB computer interface. Where a third computer system (remote user computing device) may control the MCB interface. The method of indirectly to direct using an MCB to control and view one or more computing devices that control one or more medical device, equipment, robotics, or its parts. Where each (MCB) base may control one or more equipment's via one or more networks. The secondary layer method of control where the remote user (HCP) with a third portable electronic device PED may control via direct means the one or more computer interface and emulated interface of a medical device via direct or indirect to direct connection.

DETAILED DESCRIPTION

Embodiment of the present disclosure may include a MCB 15 smart hub computing system 15 to provide IoT enhancement to medical devices 71 and a method of using such computing device to provide telemedicine ocular health and vision examination to an examinee 32 31. Where an examinee 32 31 may be new patient, existing patient, or any human. Embodiment may also include a telemedicine remote medical examination connection may be switched multiple types of RAT 2 12 49 interconnection. In some embodiments the system may allow a remote user 30 using a PED 1 portable electronic device to remotely control and remotely view one or more medical device interfaces 45 via RAT 2 12 49 and (IoT) Internet of things capabilities technology from any location 13. We devised a system and method of achieving such connection for a user 30 (health care provider 30) to provide medical examination to an examinee 32 31 independent of location 13 using an MCB 15.

Embodiment may also include a method of using one or more medical devices 71 and computing devices to deliver an indirect or direct medical examination to an examinee 32 31 independent of location 13. The proposed kit includes a series of medical devices 71 and non-medical devices 71 used herein. The (OEK 71) ocular health examination kit comprises portable ocular health and vision health medical devices 71 to be used to perform an examination to an examinee 32 31. The (OEK 71) comprises one or more computing device.

Embodiments may also include at least one of the computing devices other than a MCB 15 main control base computer. The MCB 15 comprising, emulating software, an adapter 14 69 and RAT 2 12 49 remote administration tool technology category programs and an interface 45. (FIG. 4). The (OEK 71) ocular examination kits may be assembled in any location 13 schools 70, astronaut space stations 70, emergency rooms 70, clinics, mobile clinics 70, military bases 70, aircraft carriers 70, mobile 70 or non-mobile location 13 70 by as an assistant 31 32 30. (FIG. 4) (FIG. 20).

In some embodiments, the addition of other vision examination medical devices 71 such as a portable digital phoropter 71 or subjective refractor apparatus 71 and a computing device software's may also be connected to the MCB 15 system via an emulation (FIG. 24) software. The action of connecting a computing device associated to a medical device to the MCB 15. In some embodiments, the MCB 15 may be connected to one or more remote user 30 portable electronic devices PED 1 to establishes a connection. The connection point to provide Indirect to direct 74 medical service and subjective refraction service to a human examinee 32 31 on or out of earth.

In some embodiments, the enhancement of a medical device to have IoT capabilities via RAT technology 2 12 49 and emulation software (FIG. 24) to achieve a point of connection from any remote user 30 computing device PED 1. The ocular examination kit OEK 71 may be installed inside or outside of a room 70, offices 70, mobile trailers 70, mobile exam rooms 70, kiosks 70, booths 70, astronaut space station 70 or anywhere in the world 70. (FIG. 20). The medical device kit 71 used to describe the invention will be the (OEK 71) ocular examination equipment kit. The OEK 71 contains at least one portable computing device. At least one of the portable computing devices includes a an operating system, interface 45, adapter apparatus 14 69 (AA), emulation (FIG. 24) software. The MCB 15 may connect to the one or more medical devices 71 interface 45 via wired or wireless networks 29 depending on system used. (FIG. 4;15).

In some embodiments, the (OEK 71) ocular examination equipment kit may contain at least one of an MCB 15 computing device, wireless cellphone 50 9 router 20, smartphone 21, slit-lamp 22, two iriscope 17, non-mydriatic retinal camera 16, multiple USB connectors, and a head-mount ocular camera 36 6 17 41 examination apparatus 19 (FIG. 4;23,24,25,22,20,23,26,17,16,18). The iriscope 17 may be a microscope camera used to evaluate the ocular health of an examinee 32 31. The ocular examination kit can also include a digital phoropter 71 or (subjective refractors apparatus 71), lens-meters 71, and auto refractor systems 71 to be connected and controlled from a remote user 30 and/or assistant 31 32 30. In some cases, one or more MCB 15 smart hub computing devices may or may not be added to the systems for use of adding extra medical devices 71.

In some embodiments, the MCB 15 may be a smart hub computer system 15. The MCB 15 may execute one or more software via remote or non-remote means. In some cases, one of the software's may be at least one of: an remote exam scheduling software, machine learning software, emulating software, electronic medical record software, RAT 2 12 49 remote administration tools software, and multiple ocular health cameras software's. In some embodiments, any health care provider 30 may be a remote users 30 in the on-demand service network 29. They may sign up 3 to the mobile application 12 and run a mobile application 12 on their personal electronic device PED 1 or computing device 1 (smartphone, tablet, virtual reality headset, augmented reality headset, AR/VR, smartwatch, or laptop) to view and control one or more medical device interfaces 45 and deliver a remote examination. (FIG. 2; 1,2,3,4,5,6,7) (FIG. 3).

In some embodiments, the remote user 30s PED 1 may be a computing device comprising a mobile application 12 may execute a mobile app or software that may vary depending on operating system. In some embodiments, at least one mobile application 12 may also be a DAPP decentralized application 12 running on a blockchain system for authentication. In some embodiments, the mobile application 12 facilitates connection to the (RMF 70) remote medical facility MCB 15 computing device designated for the location 13, day, and time they will provide service and payment 57 58 6 for medical service rendered. (FIG. 3; 67,55,8,9, 10,49,68). Any location 13 mobile or non-mobile comprising at least one part of the system and medical devices 71 may be called the remote medical facility (RMF 70) during our description of the invention.

In some embodiments, the (RMF 70) with their (OEK 71) will include one or more computing device interfaces 45 that may require a username 67 54 and password 55 54 for the on-demand remote user 30 to provide service on the day and time the service will be rendered (FIG. 20; 55,30,56). Payment 57 58 6 to the remote user 30 (eye doctor or health care provider 30) may be sent from examinee 32 31 to user or via from the remote medical facility to the remote user 30 (HCP). In some cases, direct payment 57 58 6 from the examinee 32 31 to the remote use may be made. (FIG. 17; 58).

In some embodiments, the remote user 30 may be any health care provider 30 including at least one of: nurse, eye doctor, physician assistant 31 32 30, medical assistant 31 32 30, assistant 31 32 30, medical doctor, Doctor of Osteopathic Medicine, optometrist, and/or ophthalmologist). The payment 57 58 6 may be made to the remote user 30 via credit card, cryptocurrency, or any other type of payment 57 58 6 method. An assistant 31 32 30 will be at the remote location 13 and will set up the ocular examination equipment Kit (OEK 71) and connect online. (FIG. 5; 31). The assistant 31 32 30 may be a (a human, nurse, medical assistant 31 32 30, doctor, optometric technician, ophthalmic technician, autonomous machine and/or any health care provider 30 31.

In some embodiments, the assistant 31 32 30 may help with the connection to the mobile application 12 and help with the connection to the on-demand remote user 30 (HCP) if needed. (FIG. 5). In cases of the same day on demand service, the request can be from facility MCB 15 computing devices to remote user 30 PED 1 computing device or from eye doctor PED 1 computing device to facility computing device depending on the application 12 setting used. (FIG. 3;67) (FIG. 20; 55,30,56).

In some embodiments, the remote user 30 may user a computing device comprising a software 38 to be able to control the computing device (MCB 15) interface 45 without having to be located at the RMF 70. In some embodiments, the remote medical facility RMF 70 may be in a mobile location 13 or a non mobile location 13. (FIG. 5) (FIG. 6; 30,29). The system interconnection is made via internet networks 29 and by one or more (RAT 29 2 12 49) remote access tools software 29 application 12 technology. The internet interconnection may be via ethernet, cellphone 50 9 wireless networks 29, WIFI 28 or another telecommunication 27 network 29.

In some embodiments, the interconnection of the on-demand remote user 30 (health care provider 30) and at least one computing device at the remote medical facility (RMF 70) may be delegated via a mobile application 2 12 or software. The mobile application 2 12 may be of centralized or a decentralized application 12 (DAPP), or website 12. Instead of a remote user 30 providing telemedicine examinations service from one fixed location 13 to a secondary fixed location 13, the remote user 30, OEK 71 and the RMF 70 may be in either stationary or non-stationary locations 13 due to the portability aspects. In some embodiments, the method of provides medical examination via a flexible, portable system combination. This method of using portability enables even a human in outer space (FIG. 21) or in a very remote area to receive telemedicine medical, ocular health and vision examination service by a remote user 30 with PED 1 independent of location 13. (FIG. 2).

In some embodiments, the RMF 70 may comprise one or more computing device that may send and receive data to and from a remote user 30 computing device PED 1 independent of location 13. In some embodiments, the medical devices 71 comprising the OEK 71 may be at least one of a digital slit-lamp 22, digital iris-cope, digital retinal camera 16 that may be controllable by a remote user 30 and/or assistant 31 32 30. The control and screen view may be assisted by a computing device (MCB 15) in the location 13 via a wired or non-wired connection. (FIG. 5;16,19,17,22, 26,14,15). The computing device (MCB 15) may execute and commission software to controls 39 one or more software interface 39 45 that controls one or more medical devices 71. (FIG. 12).

In some embodiments, as depicted-on FIG. 12 one can see a method of doing a remote cornea 40 43 fluorescein 18 staining evaluation. An assistant 31 32 30 or examinee 32 31 may instill one drop 33 of fluorescein 18 sodium dye to one or more eyes of an examinee 32 31. In some embodiments the examinee 32 31 eyes health may be examined, viewed, and recorded by a remote user 30 via real-time connection. The remote user 30 (HCP) examine for cornea 40 43 surface damages as seen via one or more interfaces 45. The data is collected via external ocular camera 6 17 41, iris cope, ocular camera 6 17 41 headset apparatus, or a slit lamp. In some embodiments the remote user 30 may be an eye doctor 30 connected via a computing device and real-time screen mirrored to location 13 vision display 50.

In some embodiments, the eye doctor may view one or more images and saved data of cornea 40 43 and conjunctival damages. In some embodiments, the eye doctor or assistant 31 32 30 may view the fluorescein 18 stained cornea 40 43 with without cobalt light filter 39 picture using real-time remote administration tool, emulating software's, screen share, screen control and screen mirror software's and an internet network 29 or network 29 connection. In some embodiments, the at least one of the evaluations is to determine if the cornea 40 43 has at least one of: superior punctate keratitis, second is staying skating rink core abrasion caused by possible PED 1 foreign body PED 1 under the upper eyelid, third is staining foreign body material metal, wood plastic or glass in the cornea 40 43, and fourth is staying cornea 40 43 abrasion or lacerations 40.

In some embodiments, the method of using (MCB 15) computing device including a (RAT 2 12 49) remote administration tool technology software or application 12 installed into its main operating system to control emulated medical device software interface 45 that control the medical device. (FIG. 18; 12,15). The method of using a computing device (MCB 15) may also comprise a browser that may serve as a remote connection to the users computing device. The possibility of using a browser with a remote connection 38 may be facilitated by an commercial or non-commercial company product if needed. The computing device (MCB 15) may be of any (OS) operating system Android, windows, or Linux depending on the computing device and may include an emulation (FIG. 24) interface 45. (FIG. 19). The remote user 30 may have any portable electronic device or computing device such as a smartphone, tablet 1, laptop 1, virtual reality headset 1, augmented reality headset 1, AR/VR 1, that may be of any operating system such as Android, Windows, Linux or any other OS. (FIG. 2).

In some embodiments, the remote user 30 computing device may execute a mobile application 12 or software to be used to connect control and view an computer interface 45 at the remote medical facility (RMF 70). (FIG. 21). The RMF 70 may be in a mobile or non-mobile location 13 on earth or off earth. The computing device (MCB 15) in the medical device interface 45 control to be interfaces at the same time by an assistant 31 32 30 and by a remote user 30 (health care provider). (FIG. 18). The remote user 30 may need to have the mobile application 12 running on a portable electronic device such as a tablet, smartphone 1, AR/VR 1, virtual reality headset 1 or augmented reality headset 1 to interconnect. The PED 1 must be connected via at least one of an internet network 29 and a telecommunication 27 network 29.

In some embodiments, the remote user 30 may comprise a computing device that may execute control and remote screen viewing of one or more computing device interfaces 45 associated with a medical device at the RMF 70. The remote user's 30 computing device or PED 1 application 12 may have RAT 2 12 49 enabling use to interconnect to the MCB 15 computing device located at the remote medical facility (RMF 70). (FIG. 2; 1,2). The remote user 30 may receive a text message authenticating access to one device with the username 67 and password 55 via the MCB (FIG. 3).

In some embodiments, the main purpose MCB 15 computing device may be direct control of one or more computing devices, access to electronic medical records software, control and view of medical device interface 45 via wired or wireless connection. In some embodiments, user computing device is to remote access and view the emulated interfaces 45 of the MCB 15 interface 45 via wired or wireless connection using a RAT 2 12 49 software. The remote user 30 may control and view one or more interfaces 45 of one or more computing devices associated and not associated to a medical device. (FIG. 5) (FIG. 18). In some embodiments, the (MCB 15) computing device may include an adapter 14 69 to be used to connect to any medical device computing device that may control any medical device, eye examination equipment, vision examination device one or any maker.

In some embodiments, the MCB 15 computing device may access a connection to achieve an internet connection via ethernet, WIFI 28, or any cellphone 50 9 wireless network 29. If the remote medical facility (RMF 70) or the center does not have its own internet service, the ocular examination equipment Kit (OEK 71) may also come with a wireless cellphone 50 9 network 29 internet router 20 to provide an internet connection to an MCB 15 system if not already built in. (FIG. 4; The remote user 30 computing device may be any PED 1 (portable electronic device) connected and used to provide telemedicine medical, ocular health examination service to an examinee 32 31. The remote user 30 may be any human, optometrist, ophthalmologist, or any health care provider 30.

In some embodiments, the examinee 32 31 may receive medical service via one or more intermediary computing devices if needed. The remote user 30 may use one or more portable electronic device as a computing device to provide the medical service to the examinee 32 31. The possible computing device may be virtual reality headset, augmented reality headset, smartphone, smartwatch, laptop, personal computers and/or tablet. (FIG. 2;1). The remote user 30 may be a health care practitioner of any kind and may delegate such task service to any human if needed. The onsite assistant 31 32 30 or examinee 32 31 may also be remote user 30 by the PED and equipment or interface 45s in some systems if needed.

In some embodiments, the MCB 15 computing device may be remotely controlled over Internet protocol network 29s using an applet running on the communication device. The remote user 30 (eye doctor) computing device (PED 1) may control one or more computing device interface 45s via one or more RAT 2 12 49 applet running. The remote user 30 may use one or more a portable electronic device PED 1 computing device (smartphone 1, tablet 1, laptop 1, virtual reality headset 1, smartwatch 1 and AR headset 1) to provide remote medical examination service to an examinee 32 31.

The RAT 2 12 49 remote administration tool technology program aids in the telecommunication 27 interconnection between one or more computing device independent of type operating system. (FIG. 19).

In some embodiments, the method of beginning a telemedicine medical service may be requested, demanded, or commissioned by a remote user 30, examinee 32 31, assistant 31 32 30, program or mobile application 12. The user computing device PED 1 may receiving or sending a message via an application 12. This variability request options aid in the on-demand remote user 30 to remote access the system. The remote user 30 may accept, decline or request (RAT 2 12 49) interconnection. The remote user 30 may also commission the MCB 15 to commission autonomous medical devices 71 if needed also.

In some embodiments, a mobile application 12 may also work by having a remote user 30 executes a search engine for a regional geolocation 13 onto an MCB 15 interface 45. The mobile application 12 to provide service or it can be via secondary third-party application 12. The mobile application 12 or website 12 may function similar to existing system like Airbnb, Uber, or Lyft, where a remote user may select from one or more location, providers or service. When the remote user 30 accepts the request, they may have to insert a username 67 54 and password 55 54 via the RAT 2 12 49 remote administration tool software to gain access to the MCB 15 computing device interface 45.

In some embodiments, the (RAT 2 12 49) remote administration tool program may be a commercial or noncommercial software installed within its system. The software may randomly generate a username 54 67 and password 55 authentication for the remote user 30 to be able to log in and connect to the MCB 15 computing device interface 45. The remote medical facility computing device may also delegate a username 54 67 and password 55 for the remote user 30 (eye doctor) 30 to connect to one or more systems if needed. This random username 67 54 and password 55 facilitate a secure connection from a remote user 30 scheduled to become a supported controller and remote viewer.

In some embodiments, the medical service may be provided to an examinee 32 31 (patient) via remote control means. By way of indirect to direct 74 connections to the medical device, the eye doctor may control the RMF 70 computing device (MCB 15) interface 45. The MCB 15 commissioned to directly control one or more computing devices interfaces 45 that control ocular health medical devices 71 and an EMR electronic medical record 11. (FIG. 23).

In some embodiments, the remote user 30 may control the system via indirect means, by operating the digital ocular camera 6 17 41 to diagnose and assess an examinee 32 31. The remote user 30 computing device may also connect to a digital slit-lamp 22 camera system remotely to refine images 53 51 and videos 53 51 for a proper remote ocular examination from a patient. An adapter 14 69 on the digital slit-lamp 22 can be added to facilitate the remote control of the slit control, click stop, filters, magnification changer, and joystick elevation knob. Some portable or non-portable slit lamps may already come with built-in robotic or electronic control of all: slit control, illumination arm, click stop, filters, magnification changer, and joystick elevation knob.

In some embodiments, the control system may be connected via an adapter 14 69 apparatus, emulating software, or run via OS compatible control software via the MCB 15 to have complete control remotely by a remote user 30 providing service. The remote user 30 may be connected to the system and may control the iris copes and slit-lamp 22 to gather video 51 53 and/or pictures 51 53 of the patient's (examinee 32 31) ocular health. In some cases, the remote user 30 may switch from the indirect to direct 74 to (direct to direct) connection method to get an alternative layer and type of connection (FIG. 24).

In some embodiments, the remote user 30 may also be at the location 13 RMF 70. The remote user 30 may be in a different room or near the location 13 of the examinee 32 31 in a possible scenario. If the remote user 30 may not be able to be at the location 13 RMF 70, an onsite or offsite assistant 31 32 30 may be delegated to be a remote user 30. If a medical device is autonomous capable, the computing device comprising the automation may be considered the assistant 31 32 30 and reference as a machine on claims. Moreover, the variability and method of use to perform a remote medical exam may be dependent on the level of evolution of the medical device in market. The controlling, viewing and executing the snap of an images or videos of the anterior segment of the eye via the (ocular camera 6 17 41) iriscope 17 and slit lamps systems may be simultaneously control by both an onsite assistant 31 32 30 and off-site remote user 30.

In some embodiments, the assistant 31 32 30 may be at the location 13 and be the remote user 30. In other scenarios the assistant 31 32 30 may be an examinee 32 31 or prior examinee 32 31. The (examinee 32 31) patient eyes may be tested for several conditions using the different lights and magnification on the ocular cameras 6 17 41. To clarify some scenarios a remote user 30 may be considered a remote controller, remote viewer, or remote delegator. The remote user 30 may review or perform a real-time ocular and retinal exam via commissioning a command to take the picture 39 and zoom 39 in and out to analyze data.

In some embodiments, the remote user 30 may also remote access a cloud 73 storage system or the memory built-in into the camera's. When the a real-time screen sharing connection is optimal, the remote user 30 may review the images via real-time screen share and control. In optional scenarios of real-time viewing and control 51 the use of iriscope 17 51 53 or slit lamps 51 53 may be used. the remote user 30 may control the lights and filters of the slit-lamp 22 and/or the iriscope 17 contraption. The filters that may be used may be at least one of a cobalt blue filters, green, red-free filters, and neutral density filters.

In some embodiments, the use of these filters using ocular health cameras may be used by the remote user 30 to gather data, diagnose, assess and treat an examinee 32 31 with an ocular condition. The iris copes, and slit lamp will be used to evaluate the health of the anterior segment of the eye as far posterior as the anterior portion of the aqueous humor. The remote user 30 (Health care provider 30 or the assistant 31 32 30) can vary the angle of illumination arm, magnification, and type of slit beams via manual or remote means using the software running inside the MCB 15. The option of the type of slit lamps beams may be from diffused, wide parallelepiped 1, narrow parallelepiped 1 optic section cornea 40 43 beam wide parallelepiped 1 narrow parallelepiped 1 to view the appropriate ocular structures.

In some embodiments, the examination may be performed by, an assistant 31 32 30 at the remote office if needed. In some embodiments, the instilling of fluorescein 18 sodium on the examinee's 32 31 or patient's eye may be examined by a remote doctor or assistant 31 32 30. In some embodiments, the view and control of the adnexa of the eye may administered by a remote user and the assistant 30 31 via the lighting filters on the digital slit-lamp 22 or iris cope to determine anomalies of the cornea 40 43 or conjunctival tissue 43 of the examinee 32.

In some embodiments, the remote user 30 (eye doctor 30 or Health care provider 30) may also control the digital slit lamp, or iris copes real-time during the examination if needed. The controller of the iriscope 17 or slit-lamp 22 will take image photos or videos to review but may also be review by remote doctor real-time or near real-time. During the iriscope 17 and slit-lamp 22 examination, the anterior segment of the eye will be examined by the assistant 31 32 30, including: Lids 43, lashes 43, cornea 40 43, conjunctiva, and anterior chamber 43. In the event of no cornea 40 43 problems, the remote doctor may instruct the assistant 31 32 30 to perform ocular pressure tonometry 26 on a patient to view intraocular pressure results. (FIG. 14).

In some embodiments, the ocular pressure tonometry 26 may be transmitted automatically to the computing device 15 (MCB 15) interface. In some embodiments, the data may be viewed by the remote user 30 eye doctor 30 via the RAT 2 12 49 remote administration tool interconnection and screen share. (FIG. 14). The remote user 30 may control one or more computing interfaces. The remote user 30 may also access, edit and quantify data via real time connection.

In some embodiments, in the event of an unstable connection, the assistant 31 32 30 can take the tonometry 26 reading and type the results to the EMR 11 software or send the results to the eye doctor 30 via text (store and forward model). (FIG. 20). At the end of the remote telemedicine remote control connection, the remote eye doctor may prescribe proper medications for the ocular conditions. All information may be edited by both remote user 30 (eye doctor) and assistant 31 32 30 in real-time. The electronic medical record (EMR 11) may be edited via one or more portable computers system via remote control and remote screen sharing technology. (FIG. 15).

In some embodiments, the on-demand remote user 30 may perform the ocular examinations remotely and may communicate with the patient via HIPAA compliant encrypted video 50 21 and voice 21 50 or voice call 27 via one or more devices. The video audio or audio call 27 may be done via the remote medical facility smartphone or any other computing device in the (OEK 71). In some embodiments, the communication 50 may be via one or more smartphone connection. The RMF may have a PED 21 that may help in the video audio connection if needed.

In some embodiments, the remote user 30 may also use headphones with a microphone to maintain clear communication with the (examinee 32 31) and use one or more telecommunication 27 networks 29. The remote user 30 (eye doctor) may communicate with the patient to gather data via various remote means. One form of gathering may be via medical device interface 45 visual and an EMR 11 or paper chart scans. In a method of payment 52 57 58 6 processing for service provided the remote user 30 may receive payment 52 57 58 6 via mobile application 12 or via a contract with the remote facility or entity which it represents. Payment 52 57 58 6 can also be made via connection to a mobile application 12 on the examinee's 32 31 smartphone or portable electronic device. (FIG. 17).

In some embodiments, the remote user 30 may send out a prescription 47 via image or email to the MCB 15 computing device or to a pharmacy, or to the patient's email. (FIG. 16). In some scenarios the remote user 30 may use a transaction hash system to validate prescription 47 send. The types of prescription 47 that may be sent by the remote user 30 may be medical prescription 47 for pills, medical prescription 47 for eyedrop 33s, medical prescription 47 eye drop 33, eyeglasses prescriptions 47, or contact lens prescriptions 47.

Embodiments may also include send the digital envelope to at least one computing device. Embodiments may also include receive a digital signature 46 from at least one computing device. Embodiments may also include send an authentication result of the digital signature 46 to the one or more computing devices. Embodiments may also include receive and sending a value of the user and examinee 32 31 information prescription 47. Embodiments may also include determine the authenticity of the value using an encryption source over one or more networks 29. Embodiments may also include concluding the medical examination of the examinee 32 31. Embodiments may also include at least one connection may include at least one of a telecommunication 27 networks 29, node 15, computer network 29, data networks 29, cellphone 50 9 wireless network 29, WIFI 28, wired network 29, short-range wireless technology, and long-range wireless technology.

In some embodiments, the MCB 15 system may also be operated by a network 29 of healthcare providers via one or more application 12 used in one or more computing PED 1. The mobile application 12 has the capabilities to have a scheduling system for each remote medical facility needing service. The MCB 15 system is built to be upgradable to provide extra medical device adaptability. Some of the equipment adaptability may be any digital phoropter 71, subjective refractor apparatus 71, digital autorefractor 71, digital refractor 71, digital lensometer 71.

The medical devices 71 may be from any company as long as inter-emulation (FIG. 24) connection is achieved properly. With the use an adapter 14 69 and software, many medical devices 71 interface 45 systems or eye examination equipment can become remotely controlled and viewed by a remote user 30 (healthcare provider 30) over a network 29. In the case of the digital phoropter or any portable digital phoropter technology 71, a remote healthcare provider may be able to control the robotic equipment inside the phoropter that changes the lenses or that changes the shape of the lenses depending on the digital phoropter technology used. (FIG. 23).

In some embodiments, a medical device 71, ocular health device 71, vision system and vision refraction system are used, the ability of the MCB 15 and adapter 14 69 being used with RAT 2 12 49 software helps in the connection to the device 71. The connection from a remote user 30 computing device to the system aids in the (IDD) indirect to direct 74 connection. The use of an MCB 15 system will aid in the IoT enhancement of billions of old or new medical devices 71. The use of the MCB 15 smart hub will enable a new and innovative way to bridge the health care practitioner 30 to a patient 32. The MCB 15 will be used to monitor, examine, screen, and diagnose patients 32 anywhere in the world independent of time and space.

In some embodiments, the method the MCB 15 system continues to be configured and evolve as a medical examination intermediary platform hub. With the era of Web 3.0 the future of health care may be a global service. The MCB 15 will continue to be enhanced to aid in the IoT access to wearable medical smart devices 71. The continued evolution having a hub to interconnect will provide medical access and service to billions worldwide at a low cost.

In some embodiments, the next step of evolution of the MCB 15 will be focused to enable the control of next level of telemedicine technology such as: telemedicine robotic 71 74, autonomous medical examination devices 71 74, telemedicine patient monitoring systems 71 74, and access to wearable medical devices 71 all using a MCB 15 computing device and smart health hub interface 45. While providing remotely access and screen viewing capabilities to a remote health care provider 30 independent of location 13. The next generation MCB 15 computing device 15 such as virtual reality headset will aid in multiple method of examination. The technology will continue to be enhanced in order to help millions of underserved people with limited access to medical services worldwide. (FIG. 24).

What is claimed is:

1. A computing device system configured to provide IoT enhancement capabilities to one or more medical devices for use in a medical examination of an examinee independent of location, the computing device system comprising:
    a first computing device located at a first location connected to a medical device; and wherein the first computing device comprises a first interface for use to view, control and operate at least a part of the medical device;
    wherein a part of the medical device comprises at least one of a component and a sensor;
    wherein the first interface may be viewed, operated, and controlled by at least one assistant at a location,
    wherein at least a part of the medical device comprises the component and the sensor controllable by the first computing device comprising a first interface;
    wherein the first interface is configured to send and receive data, instruction and commands for viewing, controlling and operating the medical device and its internal mechanics and the sensor by a second computing device;
    wherein at least a part of the first computing device is connected to the second computing device at the first location;
    wherein the second computing device comprises a second interface;
    wherein the second interface comprises a computer interface controller configured to emulate the first interface onto the second interface;
    wherein the second interface is configured to send and receive data, instruction, and commands from one or more computing devices to be viewed, controlled and operated;
    wherein the medical device and its internal mechanics and the sensor may be operated by the second computing device and a third computing device;
    the third computing device being located at a second location;
    wherein the third computing device comprises a third interface;
    wherein the third computing device and the third interface are connected to the second computing device and the second interface at the first location via one or more networks;
    wherein the second interface may be viewed, operated, and controlled by a user via the third interface;
    wherein the third interface may view, operate and control the first interface for the user via the second interface,
    wherein the first interface is controllable by the second computing device via the second interface;
    wherein the second computing device comprises the second interface that may view, operate and control one or more interface and one or more software via one interface;
    wherein the second computing device may execute a program configured to send and receive commands over one or more network to and from the third computing device to view, control and operate one or more of the interfaces and one or more of the computing devices independent of location by a remote user;

wherein the remote user is at a second location comprising the third computing device configured to connect to a computing device at the first location to administer the medical examination to the examinee at the first location by controlling one or more interfaces;

wherein the remote user includes one of: a health care provider, a human, or a machine;

wherein the examinee includes one of: a human, a patient, and a customer; and wherein the at least one assistant includes one of: the health care provider, a human, the examinee, and/or a machine.

2. The computing device system of claim 1,
wherein the medical examination comprises at least one of: a vision examination; an eye health examination; a systemic health screening; a medical history data collection; a diagnosing examination; and a treatment examination;

wherein the medical device includes a portable medical device;

wherein the vision examination includes at least one or combination of a vision acuity display, an autorefractor, a variable focus liquid lens phoropter, a liquid lens retractor, a digital phoropter, and an automatic holographic phoropter; and wherein the eye health examination includes operations of at least one of an external ocular camera, a retinal fundus camera and sensors; and wherein the systemic health screening includes using a medical dye substance to be used as a diagnosis tool.

3. The computing device system of claim 1, wherein the computing device comprises a PED portable electronic device comprising at least one or a combination of a personal computer, a smartphone, a laptop, a virtual reality headset, a smartwatch, a augmented reality headset, a VR/AR headset, and a tablet computer.

4. The computing device system of claim 1,
wherein at least one program executed onto at least one computing device interface of the computing device system includes a remote administration tool technology category software;

wherein a software executed on at least one computing system includes at least one of a screen sharing, a remote access, a messaging, a share control, a video conferencing, a file transfer, and a peer to peer computing; and wherein at least one computing device connection includes an internet connection using TCP/IP.

5. The computing device system of claim 1,
wherein the one or more networks comprises at least one of a wired connection, a wireless connection;

wherein the wireless connection includes at least one of a Bluetooth, a broadband hotspot, a modem, a router, an Ethernet, a Wi-Fi, a cellular wireless network, a Starlink, a VSAT, and a satellite;

wherein the first location includes a remote medical facility, wherein the remote medical facility includes a mobile location or a non-mobile location; and wherein the mobile location includes at least one of a vehicle, a spaceship, an astronaut, a space station, a ship, and a mobile clinic.

6. The computing device system of claim 1,
wherein the user comprises the health care provider;
wherein the health care provider includes at least one of a: human, doctor of optometry, physician assistant, nurse, ophthalmologist, medical doctor, doctor of osteopathic medicine, and doctor;

wherein the medical examination comprises a diagnosis of symptoms and signs of the examinee by the health care provider;

wherein the health care provider includes at least one of a treatment option and a prescription to the examinee for the treatment of the symptoms and sign examined;

wherein the examinee includes at least one of a human, a patient, and a customer at the first location; and wherein the user is located at the second location.

7. The computing device system of claim 1,
wherein the medical examination of the examinee includes an indirect to a direct connection RAT connection;

wherein the indirect to the direct connection RAT connection is used in a real time or a near real-time telemedicine tele-communication connection;

wherein the user performs at least one of a medical health examination, and an ocular health examination to the examinee;

wherein at least one examination aids in at least one of a diagnosis, a treatment, and a screening of a medical condition of the examinee; and wherein the user may use the medical device located at the first location to perform a telemedicine remote RAT examination of the examinee by the health care provider in the second location.

8. The computing device system of claim 1,
wherein the second computing device includes a software;
wherein the software includes an electronic medical record, a remote administration technology program, an emulation software, a screen share technology, a screen mirror technology, and an audio-video call program;

wherein the user gathers data and symptoms data of the examinee;

wherein gathering data of the examinee by the user at the second location and the at least one assistant at the first location comprises the user and the at least one assistant editing an electronic medical record via a real-time collaborative real-time editor technology;

wherein the data and symptoms data is inputted by the at least one assistant and the user synchronously and asynchronously;

wherein the examinee is monitored, tested, and examined remotely by the user for at least one of a medical health, an eye health, and a vision health examination independent of location; and wherein information may be documented via a real-time RAT connection to a computing device interface.

9. The computing device system of claim 1,
wherein the at least one assistant includes at least one of a health care provider, a human, an examinee, and a machine; and wherein the machine includes a medical device automation software for an autonomous medical device.

10. The computing device system of claim 1,
wherein at least one computing device connection comprises at least one of a wired network, a short-range wireless technology, and a long-range wireless technology; and wherein the at least one computing device connection comprises a form of encryption.

* * * * *